United States Patent
Samuelsen et al.

(10) Patent No.: US 10,905,728 B2
(45) Date of Patent: Feb. 2, 2021

(54) ***AGARICUS BLAZEI* MURILL EXTRACTS, METHODS FOR INHIBITING LEGUMAIN USING THE SAME, AND METHODS FOR TREATING TUMORS USING THE SAME**

(71) Applicant: IMMUNOPHARMA AS, Høvik (NO)

(72) Inventors: Anne Berit Calmeyer Samuelsen, Ski (NO); Lise Berven, Spydeberg (NO)

(73) Assignee: Immunopharma AS, Hovik (NO)

( * ) Notice: Subject to any disclaimer, the term of this patent is extended or adjusted under 35 U.S.C. 154(b) by 654 days.

(21) Appl. No.: 14/965,309

(22) Filed: Dec. 10, 2015

(65) Prior Publication Data

US 2016/0166623 A1    Jun. 16, 2016

Related U.S. Application Data

(60) Provisional application No. 62/090,346, filed on Dec. 10, 2014.

(51) Int. Cl.
*A61K 36/00* (2006.01)
*A61K 36/07* (2006.01)

(52) U.S. Cl.
CPC .......... *A61K 36/07* (2013.01); *A61K 2236/00* (2013.01)

(58) Field of Classification Search
CPC .................................................... A61K 36/07
USPC .................................................... 424/195.15
See application file for complete search history.

(56) References Cited

U.S. PATENT DOCUMENTS

| | | | | |
|---|---|---|---|---|
| 6,093,694 | A * | 7/2000 | Fujimiya | A61K 36/07 514/19.3 |
| 6,197,571 | B1 * | 3/2001 | Hikichi | A01H 15/00 424/93.5 |
| 2013/0142819 | A1 * | 6/2013 | Ferraz Coelho | A61K 36/07 424/195.15 |
| 2015/0359829 | A1 * | 12/2015 | Ito | A61K 36/07 514/13.3 |

FOREIGN PATENT DOCUMENTS

| | | | | |
|---|---|---|---|---|
| KR | | 720706 B1 * | 5/2007 | |
| WO | WO-2011140623 A1 * | | 11/2011 | A61K 38/16 |

OTHER PUBLICATIONS

Hetland et al. Scan. J. Immunol. 2008. vol. 68, pp. 363-370.*
Fujimiya et al. Cancer Immunol. Immunother. 1998. vol. 46, pp. 147-159.*
Ochiman et al. Planta Med. 2002. vol. 68, pp. 610-614.*
Ohno et al. Evidence-Based Complementary and Alternative Medicine. 2011. vol. 2011, 9 pages.*
Ohno et al. Biol. Pharm. Bull. 2001. vol. 24, No. 7, pp. 820-828.*

* cited by examiner

*Primary Examiner* — Qiuwen Mi
(74) *Attorney, Agent, or Firm* — Rothwell, Figg, Ernst & Manbeck, P C.

(57) ABSTRACT

Extracts of *Agaricus blazei* Murill have been found to have anti-tumor activity. In particular, a polar, high molecular weight fraction of an *Agaricus blazei* Murill extract has been found which has an inhibitory effect on legumain activity. Extracts of *Agaricus blazei* Murill can be used in a pharmaceutical composition to inhibit cysteine protease legumain in a patient suffering from a tumor thereby treating the tumor and preventing new tumors.

10 Claims, 9 Drawing Sheets

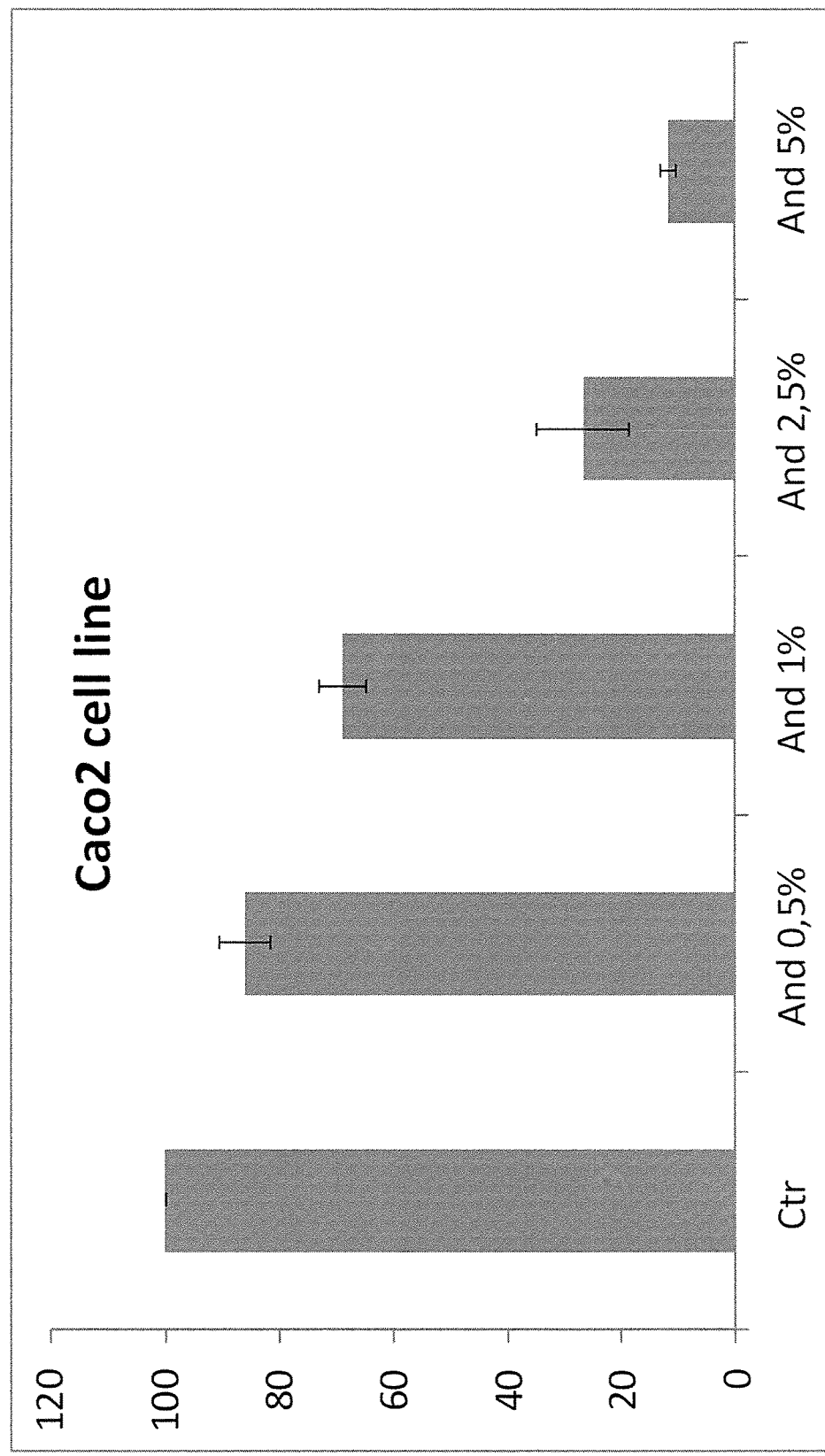

| Source | DF | prob > F | IL-1β | IL-2 | IL-4 | IL-5 | IL-6 | IL-10 | IL-17A | GM-CSF | IFN-γ | MCP-1 | TNF-α | IL-12p70 | # of small intestinal tumors | # of colon tumors | Total tumor number | Tumor load small intestine | Total tumor load colon | Tumor load colon | Total tumor load |
|---|---|---|---|---|---|---|---|---|---|---|---|---|---|---|---|---|---|---|---|---|---|
| genotype | 1 | | 0.6207 | 0.8991 | 0.5116 | 0.4550 | 0.8104 | 0.7432 | 0.7733 | 0.4863 | 0.4448 | 0.3076 | 0.1903 | 0.2530 | | | | | | | |
| Treatment | 1 | | 0.0311* | 0.8531 | 0.0704 | 0.0578 | 0.0067* | 0.4362 | 0.4371 | 0.2959 | 0.7664 | 0.0037* | 0.0013* | 0.0314* | 0.0581 | 0.1446 | 0.0210* | 0.0004* | 0.0235* | 0.0002* |
| Litter (Treatment) | 23 | | <0.0001 | 0.0017 | <0.0001 | <0.0001 | <0.0001 | 0.0034* | <0.0001* | 0.0628 | <0.0001* | <0.0001* | <0.0001* | 0.3123 | 0.0078* | 0.0364* | 0.0013* | <0.0001* | 0.0548 | <0.0001* |
| (Variance component) | | | 49% | 36% | 80% | 68% | 79% | 37% | 51% | 21% | 67% | 75% | 64% | 7% | 46% | 36% | 58% | 84% | 26% | 82% |

When litter is not considered in the model, the effect of treatment may be overestimated:

| Source | DF | prob > F | IL-1β | IL-2 | IL-4 | IL-5 | IL-6 | IL-10 | IL-17A | GM-CSF | IFN-γ | MCP-1 | TNF-α | IL-12p70 | # of small intestinal tumors | # of colon tumors | Total tumor number | Tumor load small intestine | Total tumor load colon | Tumor load colon | Total tumor load |
|---|---|---|---|---|---|---|---|---|---|---|---|---|---|---|---|---|---|---|---|---|---|
| genotype | 1 | | 0.8535 | 0.1993 | 0.0874 | 0.0601 | 0.1129 | 0.6082 | 0.2322 | 0.3193 | 0.0772 | 0.6406 | 0.9170 | 0.3639 | | | | | | | |
| Treatment | 1 | | 0.0006* | 0.6712 | 0.6909 | 0.4954 | 0.4717 | 0.0628 | 0.4172 | 0.0028* | 0.7914 | 0.0159* | 0.0019* | 0.0058* | 0.166 | 0.1027 | 0.0124 | 0.0366 | 0.0247 | 0.0006 |

AGARICUS BLAZEI MURILL EXTRACTS, METHODS FOR INHIBITING LEGUMAIN USING THE SAME, AND METHODS FOR TREATING TUMORS USING THE SAME

BACKGROUND OF THE INVENTION

Field of the Invention

The invention relates to new, purified extracts of *Agaricus blazei* Murill for treating tumors by inhibiting the activity of the cancer-related cysteine protease legumain.

Description of the Related Art

The *Agaricus blazei* Murill (AbM) mushroom, a member of the Bucidiomycetes family and a close relative to *Agaricus bisporus*, grows in the wild in the coastal Piedade area outside of São Paulo, Brazil, and has been part of the regular diet in this region. AbM was first described in 1893 by the American botanist, Charles Horton Peck (Kerrigan R. W., *Agaricus subrufescens*, a cultivated edible and medicinal mushroom, and its synonyms. Mycologia 2005; 97:12-24), and has lately been one of the most studied medicinal mushrooms. It is also known as *Agaricus subrufesence, A. rufoiegulis* and recently as *A. brasiliensis* because of its origin in a rain forest area near Piedade, Brazil (Wasser, S. P.; Didukh, M. A.; Amazonas, M. A. L.; Stamets, P.; Eira, A. F. Is a widely cultivated culinary-medicinal royal sun *Agaricus* (the himematsutake mushroom) indeed *Agaricus blazei* Murrill?*International Journal of Medicinal Mushrooms*, Reading, v. 4, n. 4, p. 267-290, 2002).

Interestingly, the frequency of serious diseases such as cancer, atherosclerosis, hepatitis, hyperlipidemia, diabetes and other geriatric diseases is lower in Piedade than in neighboring regions, supposedly due to the local high intake of AbM as a food in Piedade (Wasser S P, Weis A L: Therapeutic effects of substances occurring in higher Basidiomycetes mushrooms: a modern perspective. *Crit Rev Immunol.* 1999; 19(1):65-96)). AbM has also been found to have a beneficial effect on infections, allergy/asthma and inflammatory disorders (Hetland, G. et al., The Mushroom *Agaricus blazei* Murill Elicits Medicinal Effects on Tumor, Infection, Allergy and Inflammation through its Modulation of Innate Immunity and Amelioration of TH1 and TH2 Imbalance and Inflammation; Advances in Pharmacological Sciences, Vol. 2011).

Due to its alleged health effects, the mushroom was brought to Japan in the mid 1960's and subjected to medical research. In 1967 the mushroom was identified as *Agaricus blazei* Murill by Belgian botanist, Dr. Heinemann, and later Japanese researchers detected immuno-modulating and antitumor properties of AbM in studies in the mouse (Kawagishi H, Nomura A, Yumen T, Mizuno T, Hagiwara T, Nakamura T Isolation and properties of a lectin from the fruiting bodies of *Agaricus blazei*. Carbohydr Res. 1988 Nov. 15; 183(1): 150-4.PMID:3233595; Kawagishi H, Inagaki R, Kanao T, Mizuno T, Shimura K, Ito H, Hagiwara T, Nakamura T. Fractionation and antitumor activity of the water-insoluble residue of *Agaricus blazei* fruiting bodies. Carbohydr Res. 1989 Mar. 15; 186(2):267-73. PMID:2736561; Osaki Y1, Kato T, Yamamoto K, Okubo J, Miyazaki T., Antimutagenic and bactericidal substances in the fruit body of a Basidiomycete *Agaricus blazei*, June-17: Yakugaku Zasshi, 1994 May; 114(5):342-50, PMID:8014843; Itoh H, Ito H, Amano H, Noda H., Inhibitory action of a (1→6)-beta-D-glucan-protein complex (F III-2-b) isolated from *Agaricus blazei* Murill ("himematsutake") on Meth A fibrosarcoma-bearing mice and its antitumor mechanism. Jpn J Pharmacol. 1994; 66:265-271. [PMID: 7869611]; Ito H I, Shimura K, Itoh H, Kawade M Antitumor effects of a new polysaccharide-protein complex (ATOM) prepared from *Agaricus blazei* (Iwade strain 101) "Himematsutake" and its mechanisms in tumor-bearing mice. Anticancer Res. 1997 January-February; 17(1A):277-84. PMID:9066665). *Hericium erinaceus* and *Grifola frondosa* are two other edible Basidiomycetes mushrooms used in traditional Eastern medicine that have similar immuno-modulating and antitumor effects (Kim S P, Nam S H, Friedman M. *Hericium erinaceus* (Lion's Mane) Mushroom Extracts Inhibit Metastasis of Cancer Cells to the Lung in CT-26 Colon Cancer-Transplanted Mice. J. Agric. Food Chem., 2013, 61 (20), pp 4898-4904; Suzuki I, Itani T, Ohno N, Oikawa S, Sato K, Miyazaki T, Yadomae T. Antitumor activity of a polysaccharide fraction extracted from cultured fruiting bodies of *Grifola frondosa*. J Pharmacobiodyn. 1984 July; 7(7):492-500; Masuda Y1, Inoue H, Ohta H, Miyake A, Konishi M, Nanba H. Oral administration of soluble (i-glucans extracted from *Grifola frondosa* induces systemic antitumor immune response and decreases immunosuppression in tumor-bearing mice. Int J Cancer. 2013 July; 133(1):108-19). AbM was found to be particularly rich in different forms of β-glucans, such as β-(1→3)-, β-(1→4)- and β-(1→6)-D-glucans (Kawagishi H, Inagaki R, Kanao T, et al.: Fractionation and antitumor activity of the water-insoluble residue of *Agaricus blazei* fruiting bodies. Carbohydr Res. 1989; 186(2):267-273; Firenzuoli F, Gori L, Lombardo G: The Medicinal Mushroom *Agaricus blazei* Murrill: Review of Literature and Pharmaco-Toxicological Problems. *Evid Based Complement Alternat Med.* 2008; 5(1):3-15). These glucans, which are an integral part of the cell wall of mushrooms, exhibit potent anti-tumor activity in mouse models and cancer cell cultures (Ebina T, Fujimiya Y: Antitumor effect of a peptide-glucan preparation extracted from *Agaricus blazei* in a double-grafted tumor system in mice. Biotherapy. 1998; 11(4):259-265; Itoh H, Ito H, Amano H, Noda H: Inhibitory action of a (1→6)-beta-D-glucan-protein complex (F III-2-b) isolated from *Agaricus blazei* Murill ("himematsutake") on Meth A fibrosarcoma-bearing mice and its antitumor mechanism. Jpn J Pharmacol. 1994; 66(2):265-271; Takaku T, Kimura Y, Okuda H: Isolation of an antitumor compound from *Agaricus blazei* Murill and its mechanism of action. J Nutr. 2001; 131(5): 1409-1413), and have immunomodulatory effects on monocytes, macrophages and NK cells (Fujimiya Y, Suzuki Y, Oshiman K, et al.: Selective tumoricidal effect of soluble proteoglucan extracted from the basidiomycete, *Agaricus blazei* Murill, mediated via natural killer cell activation and apoptosis. *Cancer Immunol Immunother.* 1998; 46(3):147-159; Hetland G, Sandven P: beta-1,3-Glucan reduces growth of *Mycobacterium tuberculosis* in macrophage cultures. *FEMS Immunol Med Microbiol.* 2002; 33(1):41-45; Hetland G, Johnson E, Lyberg T, Bernardshaw S, Tryggestad A M, Grinde B: Effects of the medicinal mushroom *Agaricus blazei* Murill on immunity, infection and cancer. *Scand J Immunol.* 2008; 68(4):363-370).

In a collaboration with Shinshu Agricultural University, Nagano, Japan, a strain of AbM was chosen that had optimal properties both with regard to assumed health effects and cultivation ability. It was mixed with 15% of *H. erinaceus* and 3% of *G. frondosa* to obtain a more optimal product. In 2004 this AbM-based mixed Basidiomycetes mushroom extract was found to be the only one among all Japanese AbM extracts tested blindly in a pneumococcal sepsis mouse model at the Norwegian Institute of Public Health, Oslo, that significantly reduced bacteremia and increased the animals' survival rate (Hetland G, Johnson E, Lyberg T. Bernardshaw S, Tryggestad A M A, Grinde B. Effects of the medicinal mushroom *Agaricus blazei* murill on immunity, infection and cancer. Scand J Immunol. 2008; 68:363-370. [PMID: 18782264]). It was later trade-marked Andosan™ after the producer, Mr. Ando and chosen for further studies, which showed that it also protected against Gram-negative sepsis (Bernardshaw S, Hetland G, Grinde B, Johnson E. An extract of the mushroom *Agaricus blazei* Murill protects against lethal septicemia in a mouse model of fecal peritonitis. Shock. 2006 April; 25(4):420-5. PMID:16670646) and allergy (Ellertsen L K, Hetland G. An extract of the medicinal mushroom *Agaricus blazei* Murill can protect against allergy. Clin Mol Allergy. 2009; 7:6 (E pub). PMID: 19416507) in mouse models. These effects together with the antitumor property of the mushrooms contained in ANDOSAN™, is probably due mainly to the immuno-modulatory relative shift induced by the mushroom, from a Th2 to a predominant Th1 response (Takimoto H, Kato H, Kaneko M, Kumazawa Y. Amelioration of skewed Th1/Th2 balance in tumor-bearing and asthma-induced mice by oral administration of *Agaricus blazei* extracts. Immunopharmacol Immunotoxicol. 2008; 30:747-760. PMID: 18720167, Ellertsen & Hetland 2009). In human studies we have found that ANDOSAN™ induced increased expression of genes related to cancer defense in peripheral blood leukocytes (cell signaling and cycling and transcriptional regulation) (Grinde B, Hetland G, Johnson E Effects on gene expression and viral load of a medicinal extract from *Agaricus blazei* in patients with chronic hepatitis C infection, Int Immunopharmacol. 2006; 6:1311-1314. PMID: 16782544), and it was also shown to have anti-inflammatory properties in IBD patients and healthy individuals without any pathological findings in blood samples or clinical side effects (Førland D T, Johnson E, Sæter L, Lyberg T, Lygren I, Hetland G. Effect of an Extract based on the medicinal mushroom *Agaricus blazei* Murill on expression of cytokines and calprotectin in patients with ulcerative colitis and Crohn's disease. Scand J Immunol. 2011; 73:66-75. PMID: 21129005, Johnson E, Førland D T, Sætre L, Bernardshaw S V, Lyberg T, Hetland G. Effect of an extract based on the medicinal mushroom *Agaricus blazei* murill on release of cytokines, chemokines and leukocyte growth factors in human blood ex vivo and in vivo. Scand J Immunol. 2009; 69: 242-250. PMID: 19281536). The assumed role of AbM in immune system modulation and disease control is reviewed in Hetland et al 2011 (Hetland G, Johnson E, Lyberg T, Kvalheim G. The Mushroom *Agaricus blazei* Murill Elicits Medicinal Effects on Tumor, Infection, Allergy, and Inflammation through Its Modulation of Innate Immunity and Amelioration of Th1/Th2 Imbalance and Inflammation. Adv Pharmacol Sci 2011: 157015. PMID: 21912538).

Previously, β-glucan polysaccharide (Itoh 1994) and ergosterol containing lipid (Takaku T, Kimura Y, Okuda H, Isolation of an antitumor compound from *Agaricus blazei* Murill and its mechanism of action. J Nutr. 2001 May; 131(5):1409-13.) isolated from AbM, have been shown to have in vivo antitumor activity in transplantable tumor-bearing mouse models. Later, chemically induced carcinogenesis has been used as experimental tumor models in rodents for both hepatocarcinogenesis and colon carcinogenesis studies (Pinheiro F, Faria R R, de Camargo J L, Spinardi-Barbisan A L, da Eira A F, Barbisan L F., Food Chem Toxicol. 2003 November; 41(11):1543-50 PMID: 1296300; Ziliotto L, Pinheiro F, Barbisan L F, Rodrigues M A M. Screening for in vitro and in vivo antitumor activities of the mushroom *Agaricus blazei*. Nutrition and Cancer, 2009; 61(2), 245-250.) on possible beneficial effects of AbM extracts. The former study demonstrated hepatoprotective effect of orally administered *A. blazei* extract (Pinheiro), and the latter (Ziliotto) showed tendency to reduced dysplastic aberrant crypt formation in colon but no difference in colon tumor incidence after *A. blazei* ingestion (Ziliotto 2009).

The commercial product ANDOSAN™ is an aqueous preparation of fermented medicinal mushrooms (mainly mycelium) commonly used as a health food in Japan and Brazil. ANDOSAN™ is produced in Japan and developed and distributed by ImmunoPharma AS, Oslo, Norway. The product consists of three different mushrooms; 82.4% *Agaricus blazei* Murill (AbM, Himmematsutake in Japan, Cogumelo do Sol in Brazil), 14.7% *Hericium erinaceum* and 2.9% *Grifola frondosa*, all of which belong to the same phylum: Basidiomycota.

The stimulatory effect of ANDOSAN™ on the production of IL-1β, IL-6, IL-8, TNF-α, G-CSF and MIP-1β in monocyte-derived dendritic cells was demonstrated by Førland et al. 2010 (Førland D T, Johnson E, Tryggestad A M, Lyberg T, Hetland G: An extract based on the medicinal mushroom *Agaricus blazei* Murill stimulates monocyte-derived dendritic cells to cytokine and chemokine production in vitro. Cytokine. 2010; 49(3):245-250). Furthermore, it has been shown that ANDOSAN™ stimulation of whole blood ex vivo induced release of 17 different cytokines, chemokines and leukocyte growth factors (Johnson E, Førland D T, Saetre L, Bernardshaw S V, Lyberg T, Hetland G: Effect of an extract based on the medicinal mushroom *Agaricus blazei* murill on release of cytokines, chemokines and leukocyte growth factors in human blood ex vivo and in vivo. Scand J Immunol. 2009; 69(3):242-250). In vivo studies have demonstrated an immunological stabilizing and an anti-inflammatory effect of ANDOSAN™ both in healthy volunteers (Johnson E., et al. 2009) and in patients with inflammatory bowel disease (IBD) (Førland D T, Johnson E, Saetre L, Lyberg T, Lygren I, Hetland G: Effect of an extract based on the medicinal mushroom *Agaricus blazei* Murill on expression of cytokines and calprotectin in patients with ulcerative colitis and Crohn's disease. Scand J Immunol. 2011; 73(1):66-75), when given orally. In addition, studies in a mouse model for allergy demonstrated that this particular AbM extract may prevent allergy development and be used as a therapeutic substance against established allergies (Ellertsen L K, Hetland G: An extract of the medicinal mushroom *Agaricus blazei* Murill can protect against allergy. Clin Mol Allergy. 2009; 7:6). Although ANDOSAN™ has been well studied with regard to bioactivity, little is known about the composition of the extract and which parts of the extract are associated with the observed activities.

Colorectal cancer is the 4th most frequent type of cancer in Western societies, but the 2nd deadliest after lung cancer. The frequency of sporadic colon cancer, now accounting for about 85%, has been increasing since the second world war, most probably due to modern life style and the consumption of red meat, refined foods and alcohol, inactivity and obesity. Approximately 14% of colon cancer has a familial background, such as inflammatory bowel disease and ulcerative colitis, and 1% is caused by familial adenomatous polyposis (FAP) (see Oncolex Oncology Encyclopedia). FAP is caused by inherited mutations in the Adenomatous polyposis coli gene, apc,—a tumor suppressor gene and gate keeper for colorectal adenocarcinomas (Finlay Macrae, D. du Sart, S. Nasioulas, Familial adenomatous polyposis; Research Clinical Gastroenterology Volume 23, Issue 2 2009 197-207). Since Min (multiple intestinal neoplasia) mice have the very same apc gene mutation as do individuals with FAP (McCart A E, Vickaryous N K, Silver A. Apc mice:

models, modifiers and mutants. Pathol Res Pract. 2008; 204(7):479-90. Epub 2008 Jun. 5. Review. PMID: 18538487), they are a natural mouse model for this precancerous condition. A new Min/+ mouse strain, established at the Norwegian Institute of Public Health and bred on an A/J genetic background, may be more suited as a model for human colorectal cancer than the commonly used C57BL/6J Min/+ mouse because the novel A/J Min/+ mouse model develops a much higher number of colonic lesions. (Sødring M, Oostindjer M, Egelandsdal B, Paulsen J E1. Effects of hemin and nitrite on intestinal tumorigenesis in the A/J Min/+ mouse model. PLoS One. 2015 Apr. 2; 10(4).)

Legumain (asparaginyl endopeptidase) is a tumor-associated proteolytic enzyme that is prominently expressed in mammalian tissues such as kidney, placenta and spleen (Liu C. Sun C, Huang H, Janda K, Edgington T: Overexpression of legumain in tumors is significant for invasion/metastasis and a candidate enzymatic target for prodrug therapy. Cancer Res. 2003; 63:2957-2964) and is important for normal body weight, hematopoiesis and kidney function. Legumain knock-out mice are born healthy and fertile, but show reduced body weight, extramedullary hematopoiesis in the spleen and aberrant endo-lysosomes with development of kidney failure (Shirahama-Noda K, Yamamoto A, Sugihara K, et al.: Biosynthetic processing of cathepsins and lysosomal degradation are abolished in asparaginyl endopeptidase-deficient mice. J Biol Chem 2003; 278:33194-33199; Miller G, Matthews S P, Reinheckel T, Fleming S, Watts C: Asparagine endopeptidase is required for normal kidney physiology and homeostasis. FASEB J 2011; 25:1606-1617). High levels of legumain have been detected in solid tumors which has been correlated with enhanced tumor invasion and metastasis (Murthy R V, Arbman G, Gao J, Roodman G D, Sun X F: Legumain expression in relation to clinicopathologic and biological variables in colorectal cancer. Clin Cancer Res 2005; 11:2293-2299; Gawenda J, Traub F, Luck H J. Kreipe H, von Wasielewski R: Legumain expression as a prognostic factor in breast cancer patients. Breast Cancer Res Treat 2007; 102:1-6.). This may partially be explained by the contribution of legumain in activation of proMMP-2 and processing of cathepsins (Chen J M, Fortunato M, Stevens R A, Barrett A J: Activation of progelatinase A by mammalian legumain, a recently discovered cysteine proteinase. Biol Chem. 2001; 382(5):777-783; Mai J, Finley R L, Jr., Waisman D M, Sloane B F: Human procathepsin B interacts with the annexin II tetramer on the surface of tumor cells. J Biol Chem. 2000; 275(17):12806-12812). Legumain has also been detected on the cell surface of tumor cells (Liu C, et al. 2003) and in the tumor microenvironment (Yuan Liu, Krishna Mohan Bajjuri, Cheng Liu, Subhash C. Sinha. Targeting Cell Surface Alpha(v)beta(3) Integrins Increases Therapeutic Efficacies of a Legumain Protease-Activated Auristatin Prodrug. Mol Pharm. 2012 Jan. 1; 9(1): 168-175), where it has been shown to destroy extracellular matrix by degrading its major component, fibronectin. This suggests that legumain itself may play a direct role in extracellular matrix turnover in various pathological conditions such as tumor growth and metastasis, as well as in atherosclerosis (Morita Y, Araki H, Sugimoto T, et al.: Legumain/asparaginyl endopeptidase controls extracellular matrix remodeling through the degradation of fibronectin in mouse renal proximal tubular cells. FEBS Lett. 2007; 581(7):1417-1424). Moreover, legumain is found on tumor associated macrophages, which are important for tumor development and metastasis (Lin Y, Wei C, Liu Y, Qiu Y, Liu C, Guo F. Selective ablation of tumor-associated macrophages suppresses metastasis and angiogenesis. Cancer Sci. 2013 September; 104(9):1217-25. PMID: 23691974). Legumain is highly expressed in colorectal cancer cell lines and associated with poor outcome in colon cancer. (Haugen M H, Boye K, Nesland J M, Pettersen S J, Egeland E V, Tamhane T, Brix K, Maelandsmo G M, Flatmark K High expression of the cysteine proteinase legumain in colorectal cancer—implications for therapeutic targeting. Eur J Cancer. 2015 January; 51(1):9-17). Other known biological functions of legumain include processing of exogenous antigens within the class II MHC pathway (Manoury B, Hewitt E W, Morrice N. Dando P M, Barrett A J, Watts C: An asparaginyl endopeptidase processes a microbial antigen for class II MHC presentation. Nature. 1998; 396(6712):695-699), maturation in Toll-like receptor signaling (Sepulveda F E, Maschalidi S, Colisson R, et al.: Critical role for asparagine endopeptidase in endocytic Toll-like receptor signaling in dendritic cells. Immunity. 2009; 31(5):737-748) and autophagic-lysosomal processing of hepatocellular proteins (Øverbye A, Saetre F, Hagen L K, Johansen H T, Seglen P O: Autophagic activity measured in whole rat hepatocytes as the accumulation of a novel BHMT fragment (p10), generated in amphisomes by the asparaginyl proteinase, legumain. Autophagy, 2011; 7(9):1011-1027).

Recently, we have shown that ANDOSAN™ reduces the activity of legumain in rat macrophages (Berven L, Karppinen P, Hetland G, Samuelsen A B. The polar high molecular weight fraction of the *Agaricus blazei* Murill extract, ANDOSAN™, reduces the activity of the tumor-associated protease, legumain, in RAW 264.7 cells. J Med Food. 2015 April; 18(4):429-38). Since legumain may also partake in extracellular matrix turnover in atherosclerosis (Morita Y, Araki H, Sugimoto T, et al.: Legumain/asparaginyl endopeptidase controls extracellular matrix remodeling through the degradation of fibronectin in mouse renal proximal tubular cells. FEBS Lett 2007; 581:1417-1424.), legumain is additionally perceived as a pro-inflammatory molecule.

Legumain was first discovered in beans (Kembhavi A A, Buttle D J, Knight C G, Barrett A J: The two cysteine endopeptidases of legume seeds: purification and characterization by use of specific fluorometric assays. Arch Biochem Biophys. 1993; 303:208-213) before the mammalian version was described by Chen and co-workers in 1997 (Chen J M, Dando P M, Rawlings N D, et al.: Cloning, isolation, and characterization of mammalian legumain, an asparaginyl endopeptidase. J Biol Chem. 1997; 272(12):8090-8098). The autoactivation of the 433 amino acid prolegumain is highly pH-dependent and occurs normally at pH 3.5 to 4.5. The active enzyme has a strong specificity for hydrolysis of peptides C-terminally to asparagine (Asn), but under certain conditions, hydrolysis after aspartic acid (Asp) also occurs (Li D N, Matthews S P, Antoniou A N, Mazzeo D, Watts C: Multistep autoactivation of asparaginyl endopeptidase in vitro and in vivo. J Biol Chem. 2003; 278(40):38980-38990; Halfon S, Patel S, Vega F, Zurawski S, Zurawski G: Autocatalytic activation of human legumain at aspartic acid residues. FEBS Lett. 1998; 438(1-2):114-118). The present inventors have recently shown that at pH 4.0 the autoactivation is accelerated by glycosaminoglycans (GAGs), as well as the polyanionic polysaccharide, alginate, and in the presence of certain GAGs and alginates the autoactivation also occurs at pH 5.0 and 5.5 (Berven L, Johansen H T, Solberg R, Kolset S O, Samuelsen A B C: Autoactivation of prolegumain is accelerated by glycosaminoglycans. Biochimie. 2013; 95:772-781; Berven L, Solberg R, Truong H H T, et al.: Alginates induce legumain activity in RAW 264.7 cells and accelerate autoactivation of prolegumain. Bioactive Carbohydrates and Dietary Fibre. 2013: 2: 30-44).

The most potent endogenous inhibitors of legumain are cystatin E/M and cystatin C (Cheng T, Hitomi K, van Vlijmen-Willems I M, et al.: Cystatin M/E is a high affinity inhibitor of cathepsin V and cathepsin L by a reactive site that is distinct from the legumain-binding site. A novel clue for the role of cystatin M/E in epidermal cornification. J Biol Chem. 2006; 281:15893-15899; Alvarez-Fernandez M, Barrett A J, Gerhartz B, Dando P M, Ni J, Abrahamson M: Inhibition of mammalian legumain by some cystatins is due to a novel second reactive site. J Biol Chem. 1999; 274: 19195-19203) whereas the classic chemical inhibitor of cysteine proteases, E64, does not affect legumain activity (Chen, J M et al. 1997).

Even though animal models have demonstrated anti-tumor and anti-infective properties of β-glucans from AbM fruiting bodies (Hetland, G. et al., 2008), little is known about the active components present in the extract prepared from mushroom mycelium. Low molecular weight substances in methanol or water soluble fractions have been found to have anti-angiogenic activity (Kimura, Y., et al.; Isolation of an Anti-angiogenic Substance from *Agaricus blazei* Murill: Its Antitumor and Antimetastatic Actions, Cancer Sci, vol 95, no. 9, September 2004). WO2006133707 (U.S. Pat. No. 9,072,776) discloses pharmaceutical kits suitable for treating neoplastic diseases such as cancer comprising an anti-cancer medicament, a Basidiomycete bioactive agent in solid or liquid form, and, optionally instructions for a dosing regime. WO2006133707 does not disclose an isolated, polar, high molecular weight fraction of an *Agaricus blazei* Murill extract, a method for producing an isolated, polar, high molecular weight fraction of an *Agaricus blazei* Murill extract or a method for treating tumors associated with increased activity of legumain using an isolated, polar, high molecular weight fraction of an *Agaricus blazei* Murill extract.

The present inventors have now shown that a polar high molecular weight fraction of ANDOSAN™ has an inhibitory effect on legumain activity and can be used to treat tumors.

BRIEF SUMMARY OF THE INVENTION

The goal of the present invention is to deliver appropriate means of combating tumors, which are associated with the increased activity of legumain. Such tumors include solid tumors as well as hematological cancers such as myeloma and leukemia. A particular goal of the invention is to deliver a product capable of inhibiting the activity of the cancer-related cysteine protease legumain. This goal is attained using new, purified extracts of *Agaricus blazei* Murill.

Another object of the present invention is to provide a method for the production of a polar, high molecular weight fraction of an *Agaricus blazei* Murill extract that inhibits legumain, wherein:
- a lyophilized aqueous preparation of fermented *Agaricus blazei* Murill, optionally including *Hericium erinaceum* or *Grifola frondosa*, is extracted with dichloromethane, and
- the remaining dichloromethane-insoluble material is extracted with methanol, and
- the remaining methanol-insoluble material is treated with a concentrated aqueous solution of ethanol, possibly with 80% ethanol, and
- the remaining ethanol-insoluble material is dissolved in water and further fractionated by size, possibly by size exclusion chromatography, wherein a fraction including compounds with a relative average molecular weight in the range Mw 35.6-70.6 kDa, estimated at 50 kDa, using oat β-glucan standards is isolated as the polar, high molecular weight fraction.

A further object of the invention is an *Agaricus blazei* Murill extract obtainable by extraction with water for use in the treatment or prevention of tumors, wherein the tumor disease is related to the increased activity of legumain. The extract according to the present invention may consist of a polar, high molecular weight fraction of the *Agaricus blazei* Murill extract obtainable by the method according to present invention. The *Agaricus blazei* Murill extract according to the invention may additionally contain an extract from *Hericium erinaceum* and/or *Grifola frondosa*.

A further object of the invention is a method for modulating cellular immunity in a subject suffering from tumors associated with the increased activity of legumain. The enhancement of cellular immunity prevents the induction of cancer, reduces metastasis of cancer, activates natural killer cell activity and mediates apoptosis.

A further object of the invention is a pharmaceutical composition containing the extract according to the present invention in combination with a pharmaceutically acceptable carrier.

A further object of the invention is a combination therapy using the extract of the present invention in combination with other anti-tumor agents.

BRIEF DESCRIPTION OF THE DRAWINGS

FIG. 6: Caco2 cells in vitro treated with ANDOSAN™

FIG. 9: Cytokine and tumor statistics (Table 3)

DETAILED DESCRIPTION OF THE INVENTION

Figure 1:
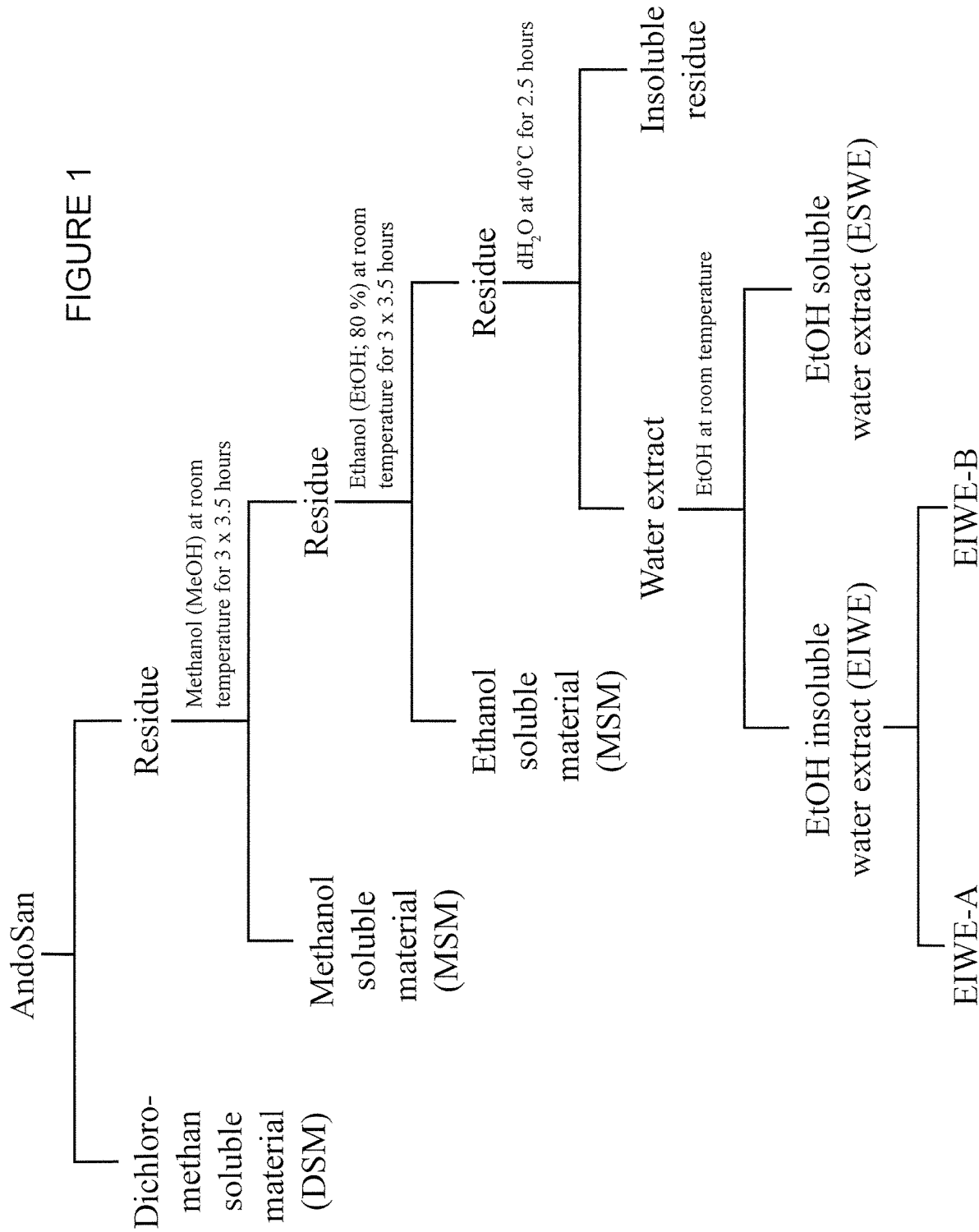
FIG. 1: Flow chart of the experimental setup.

Extracts of AbM are believed to exert their antitumor and anti-infective effects mainly through modulation of the immune system by skewing the adaptive T lymphocyte helper cells from a type 2 (pro-allergic/-asthmatic) (Th-2) response to a type 1 (antitumor, anti-infection) (Th-1) response. The immunomodulary effect is initiated by stimulation by the AbM extract of innate immune cells such as monocytes/macrophages, dendritic cells, NK cells and granulocytes via Toll-like receptor 2 and other lektin receptors (e.g. dectin-1, CD11b/18) (Fujimiya Y., et al. 1998; Bernardshaw S, Johnson E, Hetland G: An extract of the mushroom *Agaricus blazei* Murill administered orally protects against systemic *Streptococcus pneumoniae* infection in mice. Scand J Immunol. 2005; 62:393-398; Bernardshaw S, Hetland G, Grinde B, Johnson E: An extract of the mushroom *Agaricus blazei* Murill protects against lethal septicemia in a mouse model of fecal peritonitis. Shock. 2006; 25(4):420-425; Fujimiya Y, Suzuki Y, Katakura R, Ebina T: Tumor-specific cytocidal and immunopotentiating effects of relatively low molecular weight products derived from the basidiomycete, *Agaricus blazei* Murill. Anticancer Res. 1999; 19:113-118; Mizuno M, Minato K, Ito H, Kawade M, Terai H, Tsuchida H: Anti-tumor polysaccharide from the mycelium of liquid-cultured *Agaricus blazei* Murill. Biochem Mol Biol Int. 1999; 47:707-714; Tryggestad A M A, Espevik T, Ryan L, Hetland G. The medicinal mushroom *Agaricus blazei* Murill promotes NF-kB activation via stimulation of TLR2 and inhibits its activation via TLR4. J Pharm Biomed Sci, 2013, April 29(29):753-61). Furthermore, stimulation of monocyte-derived dendritic cells with the AbM-based extract, ANDOSAN™, induced upregulated expression of cell surface immune markers such as CD86, indicating increased antigen-presenting property, and CD69, showing increased activation status (Tangen J M, Tryggestad A M A, Hetland G. Stimulation of human monocytes by the medicinal mushroom *Agaricus blazei* Murill induces expression of cell surface markers associated with activation and antigen presentation, Applied Sci Reports 2014, ISSN 2054-9903, doi: 10.7243/2054-9903-1-1.). Also, an AbM polysaccharide is found to stimulate the differentiation of myeloid suppressor cells from M2 to M1 type, which mediates inhibition of tumor immune-evasion via Toll-like receptor 2 (Liu Y, Zhang L, Zhu X, Wang Y, Liu W W, Gong W, AbM polysaccharide *Agaricus blazei* Murill stimulates myeloid derived suppressor cell differentiation from M2 to M1 type, which mediates inhibition of tumour immune-evasion via Toll-like receptor 2 pathway. Immunol 2015). The present application shows that in RAW 264.7 cells, the activity of the cancer-related cysteine protease legumain is reduced by the AbM-based extract ANDOSAN™. By extracting ANDOSAN™ with solvents of increasing polarity, the fractions exhibiting the highest biological activities were identified. Unexpectedly, it was determined that the ethanol-insoluble part of the water extract obtained according to the invention, in which high molecular weight compounds such as carbohydrates and proteins were retained, is the most potent inhibitor of legumain activity. The alcohol extracts MSM and ESM and the ESWE showed no inhibiting effect.

Lyophilized ANDOSAN™ contained 2% carbohydrates, and was composed of glucose (23%), xylose (26%), arabinose (19%), galactose (10%), galacturonic acid (8%) mannose (7%), and rhamnose (7%). The monosaccharides detected correspond well with the analysis previously reported on the AbM mushroom (Kozarski M, Klaus A, Niksic M, Jakovljevic D, Helsper J P F G, Van Griensven L J: Antioxidative and immunomodulating activities of polysaccharide extracts of the medicinal mushrooms *Agaricus brasiliensis, Ganoderma lucidum* and *Phellinus linteus. Food Chemistry.* 2011; 129:1667-1675) and in addition, galacturonic acid was detected. The carbohydrates detected in ANDOSAN™ were mono and oligosaccharides, which were extracted into MSM, ESM, and partly also into the water extract, in addition to small amounts of larger polymers that were retained in the ethanol precipitated 50 kDa extract EIWE-A.

As for ANDOSAN™, the polymeric fraction EIWE-A appeared brownish in color, and 1H-NMR analysis indicated carbohydrates as the main component in addition to aliphatic structures, traces of aromatic compounds, and alkenes. The unidentified coextracted components in EIWEA may be attributed to Maillard components as a result of the production process of ANDOSAN™. Methanolysis showed that EIWE-A contained 10% carbohydrate of which 25% was glucose (Table 1). Methylation analysis revealed presence of 1→4-, 1→3-, and 1→6-linked glucose in addition to 1→3, 6-, and terminally (1→)-linked residues. Previous studies have shown that AbM contains a 1→4 α-glucan (Fujimiya, Y., et al. 1998), a 1→4/1→6 α-glucan, a 1→6 β-glucan (Fujimiya, Y., et al. 1998; Smiderle F R, Ruthes A C, van Arkel J, et al.: Polysaccharides from *Agaricus bisporus* and *Agaricus brasiliensis* show similarities in their structures and their immunomodulatory effects on human monocytic THP-1 cells. *BMC Complement Altern Med.* 2011; 11:58; Smiderle F R, Alquini G, Tadra-Sfeir M Z, Iacomini M, Wichers H J, Van Griensven U: *Agaricus bisporus* and *Agaricus brasiliensis* (1→6)-beta-D-glucans show immunostimulatory activity on human THP-1 derived macrophages. *Carbohydr Polym.* 2013; 94(1):91-99), and 1→3 β-glucan (Yu C H, Kan S F, Shu C H, Lu T J, Sun-Hwang L, Wang P S: Inhibitory mechanisms of *Agaricus blazei* Murill on the growth of prostate cancer in vitro and in vivo. *J. Nutr Biochem.* 2009; 20:753-764), and the linkages detected in EIWE-A are presumably fragments from these types of glucans, but found in lower amounts and molecular size than in the original mushroom due to degradation during the fermentation process. High amounts of terminally linked units indicate high degree of branching and/or low molecular weight. Additional carbohydrate polymers present may also contribute to the observed activity on legumain. The galacturonic acid and rhamnose residues detected may be parts of a pectin type polysaccharide, and arabinose and 1→3-linked galactans are often found as side chains in these structures (Voragen A G, Coenen G J, Verhoef R P, Schols H A: Pectin, a versatile polysaccharide present in plant cell walls. Struct Chem. 2009; 20:263-275). A 1→3-linked xylan with side chains in position 2 and 3 was also detected in EIWE-A. Trace amounts of a 1→6-linked galactan with side chains in position 2 and terminally linked mannose can be attributed to the mannogalactan previously reported for AbM (Smiderle, F. R., et al. 2013).

Figure 2A:
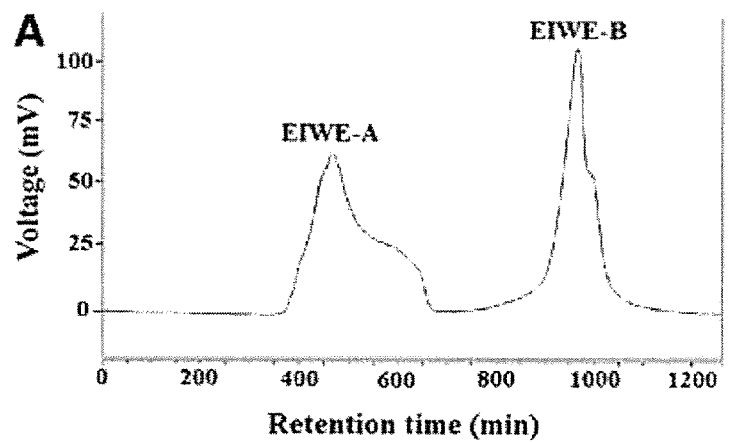
FIGS. 2A-B: Size exclusion chromatography (SEC) and size exclusion high performance liquid chromatography (SEC-HPLC). (A) Separation of EIWE fractions by size exclusion chromatography (SEC) using Sepharyl S-100 HR column. (B) Size exclusion high performance liquid chromatography (SEC-HPLC) analysis of EIWE-A and EIWE-B (EIWE-ether insoluble water extract).
Figure 2B:
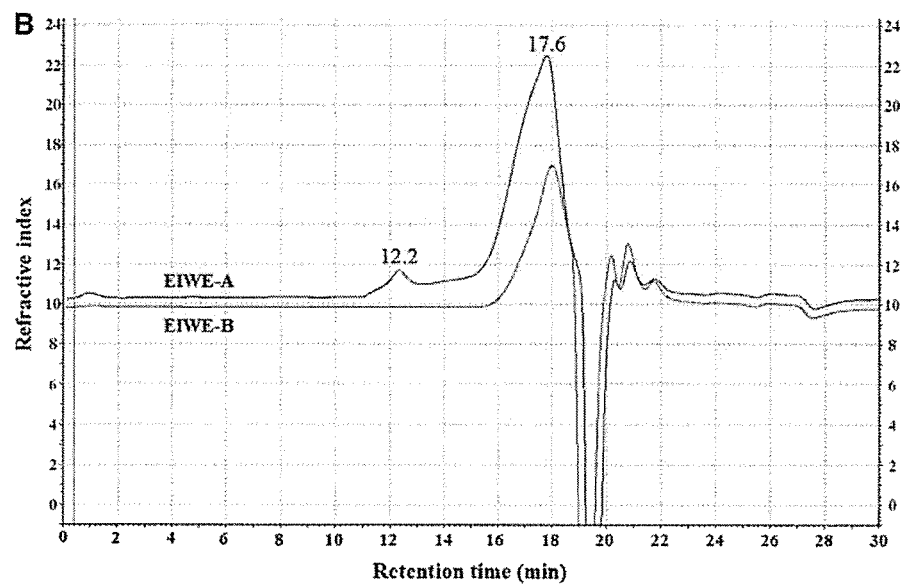

Several studies have reported that AbM is rich in biological response modulators such as β-glucans (Smiderle, F. R., et al. 2013; Ohno N, Furukawa M, Miura N N, Adachi Y, Motoi M, Yadomae T: Antitumor beta glucan from the cultured fruit body of *Agaricus blazei*. Biol Pharm Bull. 2001; 24(7):820-828), thus, the inhibiting effect of ANDOSAN™ on legumain activity may partially be caused by β-glucans and recognized by pattern recognizing receptors such as the lectin-binding site for 1-glucan in complement receptor 3 (CR3) (Czop J K, Valiante N M, Janusz M J: Phagocytosis of particulate activators of the human alternative complement pathway through monocyte beta-glucan receptors. *Prog Clin Biol Res.* 1989; 297:287-296; Vetvicka V, Thornton B P, Ross G D: Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells. *J Clin Invest.* 1996; 98(1):50-61). Toll-like receptor 2 (TLR-2) (Roeder A, Kirschning C J, Rupec R A, Schaller M, Weindl G, Korting H C: Toll-like receptors as key mediators in innate antifungal immunity. *Med Mycol.* 2004; 42(6):485-498), and dectin-1 receptor (Brown G D, Taylor P R, Reid D M, et al.: Dectin-1 is a major beta-glucan receptor on macrophages. *J Exp Med.* 2002; 196:407-412; Gantner B N, Simmons R M, Canavera S J, Akira S, Underhill D M: Collaborative induction of inflammatory responses by dectin-1 and Toll-like receptor 2. *J Exp Med.* 2003; 197:1107-1117) on RAW 264.7 cells. It has been shown that the carbohydrate content in ANDOSAN™ is only 2% of the dry weight and contains ~0.1% glucans, which is in stark contrast to previous reports, which state that dry powder of ANDOSAN™ consists of 90% carbohydrate of which 2.8% is β-glucan (Johnson, E., et al. 2009; Ellertsen, L. K. et al., 2009). The original mushroom fruiting body may contain 90% carbohydrate, but the ANDOSAN™ preparation is made of a mycelium extract. In addition, it should be noted that polysaccharides are prone to be broken down during the fermenting process which is part of the ANDOSAN™ production, resulting in minor amounts of polysaccharides and proteins in the final extract, in addition to non-identifiable fermentation products. Thus, according to our results, the beneficial biological properties of ANDOSAN™ cannot be attributed to β-glucans alone; other detected glycans may also contribute. Unidentified components present in EIWE-A correspond to the low molecular weight SEC-HPLC peak observed in both fractions EIWE-A and EIWE-B (FIG. 2B). Since only EIWE-A, and not EIWE-B, showed significant inhibitory effect on RAW 264.7 cells, it was concluded that the 50 kDa fraction of EIWE-A is responsible for the observed effect, which indicates polysaccharides and/or proteins. Trace amounts of protein components are present and need to be taken further into consideration. A few legumain inhibitors have been isolated from fungi, for example, clitocypin (MW 16.8 kDa) from *Clitocybe nebularis*(Sabotic J, Galesa K, Popovic T, Leonardi A, Brzin J: Comparison of natural and recombinant clitocypins, the fungal cysteine protease inhibitors. *Protein Expr Purif* 2007; 53(1):104-11 II) and macrocypin (MW 25 kDa) from *Macrolepiota procera* (Sabotic J, Popovic T. Puizdar V. Brzin J: Macrocypins, a family of cysteine protease inhibitors from the basidiomycete *Macrolepiota procera*. *FEBS J.* 2009; 276:4334-4345). These mushrooms belong to the same order as AbM, namely the Agaricales.

Legumain is predominantly a lysosomal enzyme. For active components to interact with the enzyme directly in the lysosomes, they may enter the cell through phagocytosis and/or macropinocytosis. Macropinocytosis, a type of endocytosis, is the invagination of the cell membrane to form and fill a pocket in a nonspecific manner, which then forms a vesicle that is 0.5-5.0 μm in diameter. The vesicle then travels into the cytosol and fuses with other vesicles such as endosomes and lysosomes (Falcone S, Cocucci E, Podini P, Kirchhausen T, Clementi E, Meldolesi J: Macropinocytosis: regulated coordination of endocytic and exocytic membrane traffic events. *J Cell Sci.* 2006; 119(Pt 22):4758-4769). Inside the lysosomes, the active components may interact directly with prolegumain or legumain. The present invention shows that both the autoactivation of prolegumain as well as the active form of the enzyme are inhibited by ANDOSAN™. Both unfractionated ANDOSAN™ and all the different ANDOSAN™ fractions showed inhibiting effects on prolegumain autoactivation. Unfractionated ANDOSAN™, EIWE, and EIWE-A were the most potent inhibitors of the active form of the enzyme. Based on these observations it was concluded that the components inhibiting autoactivation of prolegumain were present in all fractions, whereas only ANDOSAN™, EIWE, and EIWE-A contained carbohydrate polymers that inhibited active legumain directly at low concentrations. ANDOSAN™ and EIWE-A were also able to significantly inhibit legumain activity in the RAW 264.7 cells. The fact that the nonpolar fractions had no influence on legumain activity in RAW 264.7 cells indicates that the main mechanism by which ANDOSAN™ conducts its effect on these cells is by inhibiting the active form of the enzyme, rather than by inhibiting prolegumain autoactivation.

The carbohydrate content of ANDOSAN™ is 2% of the dry weight, corresponding to 0.09% β-glucan per mL ANDOSAN™, and most of the glucose is found in the most polar high molecular weight (~50 kDa) fraction of ANDOSAN™; EIWE-A. EIWE-A significantly inhibited the activity of the lysosomal protease legumain in RAW 264.7 macrophages. Both the polar and nonpolar fractions were able to inhibit prolegumain autoactivation, whereas the active form of the enzyme was most potently inhibited by the polar fractions EIWE, EIWE-A, and EIWE-B.

The mixed Basidiomycetes mushroom extract ANDOSAN™ given orally, has been shown to protect against the development of intestinal cancer in the colorectal cancer model, A/J Min/+ mice. The A/J Min/+ mouse represents a novel and improved model for colorectal cancer because adenocarcinomas are also developed in the colon and rectum (Sødring et al. 2015). Protection against the development of intestinal cancer is supported by the finding of 1) lower levels of the tumor-associated protease, legumain, in the intestines of the ANDOSAN™ treated A/J Min/+ mice, and 2) the strong, dose-dependent cytotoxic effect induced by ANDOSAN™ on the human cancer colon cell line, CaCo2 in vitro. Moreover, of the two additional mushrooms contained in ANDOSAN™, *Hericium erinaceus*, which comprises 14% of the mixed mushroom extract, has been shown to specifically inhibit metastasis of colon cancer in a transplanted mouse model (Kim et al, 2013). The other Basidiomycetes mushroom, *Grifola frondosa* comprising 3% of ANDOSAN™ also has antitumor effects in mice (Masuda et al 2013).

Legumain is produced in tumors probably by tumor-contained macrophages. Recently, it has been found that ANDOSAN™ and the polar high molecular weight fraction of it, inhibited both production of legumain by a rat macrophage cell line (RAW264.7), as well as the activation of legumain proform (Berven et al 2014). Moreover, in line with the antitumor effect of Andosan against small intestinal and colon adenocarcinoma formation, is also the in vitro cytotoxic finding of ANDOSAN™ against the human CaCo2 cell line. Previously, another AbM extract was shown to have cytotoxic effect on yet another human cancer colon cell line, HT-29, in addition to eight other human cancer cell lines (Ziliotto et al 2009). Moreover, ANDOSAN™ has also been found to have dose-dependent cytotoxic effect against murine myeloma cells in vitro (Tangen J M, Tierens A, Caers J, Binsfeld M, Olstad O K, Trøseid A M S, Wang J, Tjønnfjord G, Hetland G. Immunomodulatory effects of the *Agaricus blazei* Murill-based mushroom extract Andosan™ in patients with multiple myeloma undergoing high dose chemotherapy and autologous stem cell transplantation. A randomized, double blinded clinical study. Biomed Res Int. 2015; 2015:718539. doi: 10.1155/2015/718539. Epub 2015 Jan. 18, PMID:25664323). The antitumor activity which was observed was both dose-dependent and strong at low concentration (5%) of ANDOSAN™, strengthening the teleological/causative relationship. AbM extracts have also been shown to exhibit an apoptotic effect on leukemia cells (Gao L, Sun Y, Chen C, Xi Y, Wang I, Wang Z. Primary mechanism of apoptosis induction in a leukemia cell line by fraction FA-2-b-ss prepared from the mushroom *Agaricus blazei* Murill. Braz J Med Biol Res. 2007 November; 40(11):1545-55. PMID:17934651), which was also was the mechanism of death of CaCo2 cells incubated with ANDOSAN™.

In the in vivo situation, the components in ANDOSAN™ interact with the intestinal microbiota, which may produce other biologically active metabolites that may affect the host. Since cereal β-glucans are found to alter gastrointestinal microbiota and microbial activity in pigs (Metzler-Zebeli, B. U., R. T. Zijlstra, R. Mosenthin, and M. G. Gänzle. 2011. Dietary calciumphosphate content and oat β-glucan influence gastrointestinal microbiota, butyrate-producing bacteria and butyrate fermentation in weaned pigs. FEMS Microbiol. Ecol. 75:402-413; Metzler-Zebeli B U I, Zebeli Q. Cereal β-glucan alters nutrient digestibility and microbial activity in the intestinal tract of pigs, and lower manure ammonia emission: a meta-analysis. J Anim Sci. 2013 July; 91(7):3188-99. doi: 10.2527/jas.2012-5547. PMID: 23572264), such polysaccharides and other components in ANDOSAN™ may have influenced the composition and activity of microbiota in the A/J Min/+ mice in our experiments. Furthermore, substances in the mushroom extract may be taken up across the intestinal wall by microfold (M) cells and DC, as shown for β-glucans in murine models (Chan Y. Chang T, Chan C H, Yeh Y C, Chen C W, Shieh B, Li C. Immunomodulatory effects of *Agaricus blazei* Murill in Balb/cByJ mice. Journal of Microbiology, Immunology & Infection 2007 June; 40(3):201-8; Firenzuoli F, Gori L, Lombardo G. The Medicinal Mushroom *Agaricus blazei* Murill: Review of Literature and Pharmaco-Toxicological Problems. Evid Based Complement Alternat Med 2008 March; 5(1):3-15.) (Coombes J L, Powrie F. Dendritic cells in intestinal immune regulation. Nat Rev Immunol 2008 June; 8(6):435-46). Similar to β-glucan, other biologically active mushroom-derived molecules may further be transported by DC to lymphocytes in gut-associated lymphoid tissue (GALT), e.g. Peyers' patches, but also circulated in blood in rodents (Ikuzawa M, Matsunaga K, Nishiyama S, Nakajima S, Kobayashi Y, Andoh T, Kobayashi A, Ohhara M, Ohmura Y, Wada T. Fate and distribution of an antitumor protein-bound polysaccharide PSK (Krestin). Int J Immunopharmacol 1988; 10(4):415-23; Sakurai T, Hashimoto K, Suzuki I, Ohno N, Oikawa S, Masuda A, Yadomae T. Enhancement of murine alveolar macrophage functions by orally administered betaglucan. Int J Immunopharmacol 1992 July; 14(5):821-30). Interestingly, AbM extract has been found to preserve the intestinal nerve complex (jejunal myenteric plexus), which is important for the gastro-intestinal function, in old rats (de Santi-Rampazzo A P et al, Aqueous extract of *Agaricus blazei* Murrill prevents age-related changes in the myenteric plexus of the jejunum in rats. Evidence-based complementary and alternative medicine vol 2015, article ID 287153).

Serum cytokines seemed not to affect the local antitumor activity of ANDOSAN™ in the intestines. However, local cytokines in the intestinal mucosa may play a role and ANDOSAN™ may bring about a shift towards Th1 relative dominance locally, as we have observed previously ex vivo in spleen cells harvested from ANDOSAN™ treated Balb/c mice in the allergy model (Ellertsen & Hetland, 2006). Since the serum cytokine levels were unchanged between the untreated A/J Min/+ mice and untreated wild type mice, serum cytokine levels probably do not readily reflect carcinogenesis or tumor load in the intestinal tract. The increased levels of pro-inflammatory cytokines observed after ANDOSAN™ treatment of wild-type mice but not after such treatment of A/J Min/+ mice, illustrates a fundamental difference between these mouse strains with respect to response to danger signals such as β-glucans and other immunomodulatory substances in ANDOSAN™. This raises the question whether there also is a difference between FAP patients and healthy humans in the reaction to danger signals. If so, one may speculate that the FAP apc gene mutation also is coupled to an immunological defect.

The evidence for a link between inflammation and colorectal cancer is increasing (Hopkins M H, Flanders W D, Bostick R M. Associations of circulating inflammatory biomarkers with risk factors for colorectal cancer in colorectal adenoma patients. Biomark Insights. 2012; 7:143-50. PMID: 23170065). Pro-inflammatory markers, such as C-reactive protein, TNF-α, and IL-6, are elevated in colorectal cancer patients (Nikiteas N I, Tzanakis N, Gazouli M, et al. Serum IL-6, TNFα and CRP levels in Greek colorectal cancer patients: prognostic implications. World J Gastroenterol. 2005; 11(11):1639-43; Groblewska M M B, Wereszczynska-Siemiatkowska U, Kedra B, Lukaszewicz M, Baniukiewicz A, Szmitkowski M. Serum interleukin 6 (IL-6) and C-reactive protein (CRP) levels in colorectal adenoma and cancer patients. Clin Chem Lab Med. 2008); 46(10):1423-8), and blocking of TNFα in mice is shown to reduce colorectal carcinogenesis associated with chronic colitis (Popivanova B K1, Kitamura K, Wu Y, Kondo T, Kagaya T, Kaneko S, Oshima M, Fujii C, Mukaida N. Blocking TNF-α in mice reduces colorectal carcinogenesis associated with chronic colitis. J Clin Invest. 2008 February; 118(2):560-70. PMID:18219394). Moreover, the use of NSAIDs reduced sporadic colorectal cancer recurrence in clinical trials (Bertagnolli M. Chemoprevention of colorectal cancer with cyclooxygenase-2 inhibitors: two steps forward, one step back. Lancet Oncol. 2007; 8(5):439-43).

Previously, reduced levels of pro-inflammatory serum cytokines were found in patients with IBD, of which UC is a chronic autoimmune disease that is a risk factor/predisposes for colon cancer. In a recent placebo-controlled clinical study in IBD patients with UC, improved clinical effects of ANDOSAN™ were found after 3 weeks in this pre-colon cancer condition without side-effects (Therkelsen S P, Hetland G, Lyberg T, Lygren I, Johnson E. Effect of a medicinal *Agaricus blazei* Murill based mushroom extract on symptoms, fatigue and quality of life in patients with ulcerative colitis in a blinded placebo-controlled prospective study. Submitted for publication, December 2015). In another recent clinical placebo-controlled study in which ANDOSAN™ was given as add-on treatment to chemotherapy and stem cell transplantation for patients with multiple myeloma, the mushroom extract was found to reduce serum levels of pro-inflammatory cytokines IL-1 receptor antagonist and IL-7, upregulate immune genes, including HLA for increased antigen-presentation, increase number of immune cells (dendritic cells and Tregs), and it tended to prolong time to new treatment (Tangen J M, Tierens A, Caers J, Binsfeld M, Olstad O K, Trøseid A M, Wang J, Tjønnfjord G E, Hetland G. Immunomodulatory effects of the *Agaricus blazei* Murrill-based mushroom extract ANDOSAN™ in patients with multiple myeloma undergoing high dose chemotherapy and autologous stem cell transplantation: a randomized, double blinded clinical study. *Biomed Res* Int. 2015; 2015:718539. PMID: 25664323).

In the present application, tumors related to the increased activity of legumain are to be understood as neoplasms, which are clinically correlated with the increased expression and/or activity of legumain. This group includes but is not limited to solid tumors (e.g. fibrosarcoma, hepatocarcinoma, ovarian cancer, colorectal cancer, prostate cancer, lung cancer and colon cancer) and also includes hematological cancers such as multiple myeloma and leukemia.

The extract according to the present invention can be combined with pharmaceutically acceptable carriers and excipients including but not limited to preservatives, binders, lubricants, encapsulating agents, stabilizers, wetting agents, sweeteners, adjuvants, thickeners, dispersants, solubilizing agents and buffers which are known in the art. The composition can be in the form of a solid, liquid, or powder. Suitable pharmaceutically acceptable agents include but are not limited to: Ringer's solution, Hank's balanced salt solution, sterile buffered physiological saline; glycerin; talc; cyclodextrin; oils such as olive, sesame, soybean, cottonseed, corn, petrolatum, mineral or peanut oil; fatty acid amines; fatty acid esters such as ethyl oleate and isopropyl myristate; triglycerides; saccharides such as lactose, sucrose, mannitol, sorbitol; sodium saccharine; starches derived from vegetables such as corn, wheat, rice, or potato; cellulose such as methylcellulose, hydroxypropylmethylcellulose, or sodium carboxymethylcellulose; rubber such as gum arabic or tragacanth; proteins such as gelatin, pectin or collagen: cross-linked polyvinyl pyrrolidone, agar, alginic acid or salts thereof; magnesium stearate; stearic acid; phospholipids; polyoxyethylene, benzyl alcohol; magnesium carbonate; tragcanth; wax; cocoa butter; colorants; flavorings; propylene glycol; fatty alkali metal, detergents including cationic, anionic, nonionic, and amphoteric detergents; lecithin and polyethylene sorbitan fatty acid esters. The extract can be combined with a delivery vehicle such as a liposome, micelle and/or microsphere.

The pharmaceutical composition can be in any pharmaceutically acceptable form, including but not limited to: tablet, capsule, liquid, gel, syrup, slurry, suspension, lozenge, spray, inhalant, balm, cream, ointment, foam, aerosol, implant, suppository, transdermal patch, solution, emulsion, chewing gum, dry powder or granules, and pastille.

The extract according to the present invention can be administered with at least one other anti-tumor agent simultaneously or sequentially. Suitable anti-tumor agents include but are not limited to anti-angiogenic agents, alkylating agents (e.g. nitrogen mustards such as melphalan, nitrosoureas, alkyl sulfonates, triazines, ethylenimines), antimetabolite (e.g. 5-fluorouracil (5-FU), 6-mercaptopurine (6-MP), capecitabine, cytarabine, floxuridine, fludarabine, gemcitabine, hydroxyurea, methotrexate, pemetrexed), anti-tumor antibiotics (e.g. daunorubicin, doxorubicin, epirubicin, idarubicin, actinomycin-D, bleomycin, mitomycin-C, mitoxantrone), topoisomerase inhibitors, mitotic inhibitors (e.g. paclitaxel, docetaxel), corticosteroids (e.g. prednisone, methylprednisolone, dexamethasone), tyrosine kinase inhibitors, proteasome inhibitors, monoclonal antibodies, stem cell transplants and other agents which stimulate the immune system (e.g. interferon, interleukin). The extract according to the present invention and the anti-tumor agent can be packaged together as a single composition or as a kit with separate containers containing the extract and one or more anti-tumor agents.

The extract according to the present invention can be administered by any suitable route including but not limited to oral including sublingual and buccal, rectal, parenteral, transdermal, subcutaneous, nasal, intravenous, and pulmonary. The extract is preferably adminstered orally or parenterally.

The extract is administered in a pharmaceutically effective amount which is determined taking into account the subject's age, weight, sex, and medical condition: and the route of administration. Oral compositions will usually contain higher amounts of the extract (e.g. 0.1-75% by weight) than parenteral compositions (e.g. 0.1-25%). The optimal course of treatment (e.g. the number of doses of the extract given per day and the number of treatment days) can be determined by one skilled in the art using conventional treatment determination tests such as determining the serum cytokine levels and tumor load. Generally, the daily dosage regimen for an oral composition would be about 0.001 to about 100 mg of the lyophilized extract per kg of body weight or 10-100 ml of the liquid extract administered daily as a single dose or as a divided dose. Treatment will usually be for 10-60 days.

The contents of all of the aforementioned references are incorporated herein by reference. The invention is further illustrated by the following examples, which should not be construed as a limitation of the scope of the present invention.

Example 1. Production of Extracts

Extraction
ANDOSAN™ was provided by ImmunoPharma AS (Oslo, Norway). The brownish-colored product was a fermented extract that was composed of 82.4% *Agaricus blazei* Murill (AbM) (jap.: Himematsutake), 14.7% *Hericium erinaceum* (Yamabushitake)(Adachi Y, Okazaki M, Ohno N, Yadomae T: Enhancement of cytokine production by macrophages stimulated with (1→3)-beta-D-glucan, grifolan (GRN), isolated from *Grifola frondosa*. Biol Pharm Bull. 1994; 17:1554-1560) and 2.9% *Grifola frondosa* (Maitake)

(Lee E W, Shizuki K, Hosokawa S, et al.: Two novel diterpenoids, erinacines H and I from the mycelia of *Hericium erinaceum*. Biosci Biotechnol Biochem. 2000; 64:2402-2405). The lipopolysaccharide (LPS) content of ANDOSAN™ was found, using the Limulus amebocyte lysate test (COA-MATIC Chroma-LAL; Chromogenix, Falmouth, Mass., USA) with a detection limit 0.005 EU/mL (1 EU=0.1 ng/mL) to be a miniscule concentration of <0.05 pg/mL) (Johnson, E., et al., 2009). Lyophilized ANDOSAN™ (30 g) was extracted (see flow diagram FIG. 1) with dichloromethane (3×200 mL) by gentle stirring for 3 hours at ambient temperature and filtered to recover the dichloromethane insoluble material (DIM). The dichloromethane soluble material was designated DSM. DIM was treated with methanol (5×200 mL), and both DSM and the methanol soluble material (MSM) were concentrated under reduced pressure and dried in air. The remaining methanol insoluble material (MIM) was then treated with 80% ethanol (6×200 mL), concentrated under reduced pressure, air-dried and designated ESM (ethanol soluble material). The remaining ethanol insoluble material (EIM) was dissolved in 500 mL $dH_2O$ and incubated at 40° C. for 2.5 h. High molecular components were then precipitated by adding 2× sample volume 96% ethanol and left at 4° C. over night, then separated by centrifugation at 1750 g for 30 min. The precipitate and supernatant were designated EIWE (ethanol insoluble water extract) and ESWE (ethanol soluble water extract), respectively. EIWE was washed twice with ethanol, and ESWE and EIWE were dried free of ethanol before they were dissolved in 200 mL $dH_2O$ and lyophilized.

In one embodiment, ANDOSAN™ was lyophilized with a yield of 4.5 mg dry material/mL. The lyophilized material appeared as a brown, finely powdered product, and it was extracted with solvents with increasing polarity. ESWE had the largest yield (31.5%) followed by ESM (24.5%), MSM (17.0%), EIWE (16.0%) and DSM (0.5%). The insoluble residue constituted 10.5%. The low yield of DCME prevented further experimental focus on this extract.

Size Exclusion Chromatography

EIWE was further fractionated by size. Two fractions were obtained by size exclusion chromatography (SEC) (FIG. 2A) using a column with MW fractionation range 1-100 kDa for globular proteins. Size exclusion chromatography was performed using a Sephacryl S100 HR 26/100 column (molecular weight[MW] fractionation range 1-100 kDa for globular proteins; Amersham Pharmacia Biotech Inc.) coupled to a P-50 Pump (Amersham Pharmacia Biotech Inc., Piscataway, N.J., USA), LKB Superfrac fraction collector (Amersham Pharmacia Biotech Inc.) and an RID-6A refractive index detector controlled by Chromeleon version 7.0 software. Samples (5 mL, dry powder dissolved in $dH_2O$ to 4 mg/mL concentration) were injected, and the column was eluted with $dH_2O$ (filtered through 45 μm filter, gassed with helium; 0.5 mL/min), at ambient temperature. The fractions were designated EIWE-A and EIWE-B.

Size Exclusion High Performance Liquid Chromatography

The fractions were further analyzed using size exclusion high-performance liquid chromatography (SEC-HPLC). Size exclusion high-performance liquid chromatography (SEC-HPLC) was performed using a TSKgel G3000 $PW_{XL}$, column (TOSHO Co., Inc., Tokyo, Japan) and a TSKgel $PW_{XL}$ guard coupled to a PWLaChrom Elite L-2130 Pump (Hitachi High Technologies America, Inc., Pleasanton, Calif., USA), L-2200 autosampler and an L-2490 refractive index detector controlled with the EZChrom Elite software. The column was eluted with 50 mM $Na_2SO_4$ (0.5 mL/min) at ambient temperature, and samples (95 μL, dry powder dissolved in 50 mM $Na_2SO_4$ to concentration 1 mg/mL) were injected. Relative average molecular weights (MW) were estimated using oat β-glucan standards in the range MW 35.6-70.6 kDa (Megazyme International Ireland Ltd, Bray, Ireland) and Polymer Standard Service software (PSS WinGPC scientific V 6.20 GmbH, Mainz, Germany).

SEC-HPLC analysis of EIWE-A and EIWE-B (FIG. 2B) showed that both fractions contained components eluted after 17.6 min, which is in the lower molecular weight region of the column. A small additional peak was detected at 12.2 min in EIWE-A, indicating the presence of higher molecular weight compounds present in this fraction. Relative average molecular weight (MW) was estimated to be 50 kDa using oat β-glucan standards.

Example 2. Carbohydrate Characterization of Obtained Extracts

β-glucans are assumed to be active components in AbM, the main mushroom from which ANDOSAN™ is extracted, and thus further studies were focused on the analysis of carbohydrates in the different fractions of ANDOSAN™.

The monosaccharide composition and carbohydrate content was determined by gas chromatography of the trimethylsilylated (TMS) derivatives of the methyl-glycosides obtained by methanolysis of the polymers using 3 M HCl in anhydrous methanol at 80° C. for 24 h (Chambers R E, Clamp J R: An assessment of methanolysis and other factors used in the analysis of carbohydrate-containing materials. Biochem J. 1971; 125:1009-1018). The TMS derivatives were analyzed by capillary gas chromatography on a Focus GC (Thermo Scientific, Milan, Italy). Mannitol was included as an internal standard throughout the procedure.

Linkage elucidation was performed by methylation analysis carried out using the method of Cicanu and Kerek (Ciucanu I, Kerek F: A simple and rapid method for the permethylation of carbohydrates. Carbohydrate Research 1984; 131:209-217). The methylation procedure was followed by GC-MS analysis of the derived partially methylated alditol acetates using a GCMS-QP2010 (Shimadzu, Kyoto, Japan) attached to a Restek Rxi-5MS (30 m; 0.25 mm i.d.; 0.25 μm film) column. The injector temperature was 280° C., the ion source temperature 200° C. and the interface temperature 300° C. The column temperature was 80° C. when injected, then increased with 10° C./min to 140° C., followed by 4° C./min to 210° C. and then 20° C./min to 300° C. Helium was the carrier gas (pressure control: 80 kPa). The compound at each peak was characterized by an interpretation of the characteristic mass spectra and retention times in relation to standard sugar derivatives. Effective carbon-response factors were applied for quantification (Sweet D P, Shapiro R H, Albersheim P: Quantitative analysis by various G.L.C. response-factor theories for partially methylated and partially ethylated alditol acetates. Carbohydr Res. 1975; 40:217-225).

The carbohydrate content and monosaccharide composition are shown in Table 1. The lyophilized ANDOSAN™ contained 2% carbohydrate, corresponding to 0.09% mg β-glucan per ml ANDOSAN™, whereas MSM, ESM, ESWE, and EIWE contained 5.7%, 1.6%, 1.7%, and 6.3% carbohydrate, respectively. Due to limited solubility in methanol and ethanol, the carbohydrates detected in MSM and ESM were monosaccharides and disaccharides rather than polymers, and likewise in the ethanol soluble water extract (ESWE). The carbohydrates present in EIWE, on the other hand, were constituents of polymers (Table 2). EIWE contained the highest amount of glucose (23%). The carbohydrate contents of fractions EIWE-A and EIWE-B, were 9.7% and 0.4%, respectively (Table 1). Of total carbohydrate contents, EIWE-A contained 25% glucose, and HPLC analysis revealed that high molecular weight components were present in EIWE-A, rather than EIWE-B (FIG. 2B). Due to the high content of glucose in EIWE-A, glycosidic linkage analysis was performed on this fraction. Glucose appeared mainly as terminally-linked units (17% of total carbohydrate), but also 1→4-, 1→3-. 1→6-, and 1→3,6-linked glucose units were found, suggesting the presence of glucans (Table 2). Terminal xylose constituted about 11%, whereas the content of 1→3-linked xylose was 9% in addition to branching in O-2 and O-4. Terminally linked mannose was found in addition to galactose residues that were 1→6 and 1→2,6-linked, terminally linked, and 1→3-linked, indicating the presence of galactans. Also detected was a considerable amount of terminal arabinose (9%), in addition to small amounts of terminal, 1→2-linked and 1→2,3-linked rhamnose.

Example 3. Effects of Obtained Extracts on Legumain Activity in RAW 264.7 Cell Cell Culturing and Stimulation The murine macrophage-like cell line, RAW 264.7 (American Type Culture Collection [ATCC], Rockville, Md., USA) was cultured in Dulbecco's modified Eagles medium (DMEM; Life Technologies, Paisley, UK) supplemented with 10% fetal bovine serum gold, 1 mM sodium pyruvate (PAA Laboratories GmbH, Pasching, Austria), 100 U/mL penicillin, and 100 µg/mL streptomycin (Sigma-Aldrich, St. Louis, Mo., USA). Cells were maintained at 37° C. with 5% $CO_2$ in a humidified incubator. The cells were seeded in 6-well plates at a density of $5 \times 10^5$ cells per well ($2.5 \times 10^{-5}$ cells/mL) 24 h prior to stimulation with unfractionated ANDOSAN™, MSM, ESM, ESWE. EIWE, EIWE-A or EIWE-B) with or without Polymyxin B (10 µg/mL) at various concentrations in serum-free media and harvested after 48 h.

TABLE 1

The carbohydrate content and percentage distribution of monosaccharides in the carbohydrates detected in the extracts

| Name of Fraction | Unfractionated ANDOSAN ™ | MeOH extract (MSM) | EtOH extract (ESM) | ESWE | EIWE | EIWE-A | EIWE-B |
|---|---|---|---|---|---|---|---|
| Carbohydrate content | 2.0 | 5.7 | 1.6 | 1.7 | 6.3 | 9.7 | 0.4 |
| Arabinose | 19.4 | 11.1 | 31.4 | 19.4 | 10.6 | 9.2 | Trace |
| Galactose | 10.0 | 16.6 | 2.4 | 8.5 | 17.3 | 16.7 | Trace |
| Galacturonic acid | 8.3 | 13.2 | 0.3 | Trace | 11.6 | 12.6 | Trace |
| Glucose | 23.0 | 21.8 | 31.3 | 17.9 | 22.7 | 24.7 | 6.4 |
| Glucuronic acid | Trace | 2.1 | 8.3 | 0.6 | 3.0 | n.d* | n.d* |
| Mannose | 6.8 | 9.8 | 1.1 | 7.4 | 9.5 | 11.4 | Trace |
| Rhamnose | 6.8 | 6.6 | 6.1 | 8.0 | 6.2 | 5.4 | n.d* |
| Ribose | n.d* | n.d.* | Trace | Trace | n.d* | n.d* | n.d* |
| Xylose | 25.6 | 18.7 | 19.0 | 38.2 | 19.1 | 20.0 | 93.6 |

*n.d. = not detectable

TABLE 2

Binding pattern of carbohydrates in EIWE-A

| | % of total carbohydrates |
|---|---|
| T-Araf | 9.2 |
| T-Fucp | Trace |
| 1→3 Fucp | Trace |
| T-Glcp | 13.3 |
| 1→3 Glcp | 2.0 |
| 1→4 Glcp | 5.7 |
| 1→6 Glcp | 3.3 |
| 1→3,6 Glcp | Trace |
| 1→4,6 Glcp | Trace |
| T Galp | 8.3 |
| 1→3 Galp | 8.4 |
| 1→6 Galp | Trace |
| 1→ 2,6 Galp | Trace |
| 1→ 2,3 Galp | Trace |
| T Manp | 11.4 |
| T Rhap | 2.0 |
| 1→2 Rhap | 3.4 |
| 1→2,3 Rhap | Trace |
| T Xylp | 11.0 |
| 1→3 Xylp | 9.0 |
| 1→2,3 Xylp | Trace |
| 1→2,4 Xylp | Trace | p = pyranose,
f = furanose

Harvesting of Cell Lysates

Cell lysates were obtained by washing adherent cells in 1×PBS (phosphate buffered saline) before adding lysis buffer (100 mM sodium citrate, 1 mM disodium-EDTA, 1% n-octyl-β-D-glucopyranoside, pH 5.8). After 3 cycles of freezing (−70° C.) and thawing (30° C.), the cell lysates were centrifuged at 10,000 G for 10 min, and the supernatants were frozen at −70° C. or applied directly to enzyme activity analyses. Total protein concentrations in cell lysates were measured by the procedure described by Bradford (Bradford M M: A rapid and sensitive method for the quantitation of microgram quantities of protein utilizing the principle of protein-dye binding. Anal Biochem. 1976; 72:248-254) and performed according to the manufacturer (Bio-Rad Laboratories, Hercules, Calif. USA) in a microplate reader. Wallac Victor 3 (PerkinElmer, Waltham, Mass., USA), measuring absorbance at 595 nm. Bovine serum albumin (0-400 µg/mL; Sigma-Aldrich) was used to establish a standard curve for the calculation of total protein concentrations in cell lysates. All measurements were performed in duplicate.

Active Legumain and Preparation and Autoactivation of Prolegumain

Active legumain isolated from bovine kidney (Yamane T, Takeuchi K, Yamamoto Y. et al.: Legumain from bovine kidney: its purification, molecular cloning, immunohistochemical localization and degradation of annexin II and vitamin D-binding protein. Biochim Biophys Acta. 2002;

1596(1):108-120) was provided by Harald Thidemann Johansen, School of Pharmacy. Prolegumain (200 ng/mL) was obtained from conditioned media of HEK 293 cells stably transfected with full-length cDNA for human legumain in pcDNA3.1 vector (designated M38L cells) (Berven, L., et al., 2013; Smith R, Johansen H T, Nilsen H, et al.: Intra- and extracellular regulation of activity and processing of legumain by cystatin E/M. Biochimie. 2012; 94: 2590-2599). The concentration of secreted prolegumain was determined by enzyme-linked immunosorbent assay (ELISA) as described below. PD-10 Desalting Columns prepacked with SEPHADEX™ G-25 (GE HealthCare, Little Chalfont, United Kingdom) were used for buffer exchange of conditioned serum-free DMEM medium from M38L cells containing secreted prolegumain (200 ng/mL) to sodium acetate buffer pH 4.0 (200 mM sodium acetate and 4 mM Na-EDTA). Unfractionated ANDOSAN™, MSM, ESM, ESWE, EIWE, EIWE-A, or EIWE-B were dissolved in 0.9% NaCl and active legumain or prolegumain was incubated at room temperature or 37° C., respectively, in the presence of the different fractions or 0.9% NaCl (control) before legumain activity measurements.

Enzyme-Linked Immunosorbent Assay

Established ELISA procedures were performed to determine the concentrations of prolegumain (DY4769; R&D Systems, Minneapolis, Minn. USA) in conditioned media from M38L cells.

Legumain Activity Assay

The proteolytic activity of legumain was measured by cleavage of the legumain specific fluorogenic substrate Z-Ala-Ala-Asn-AMC (Bachem AG, Switzerland) as described (Johansen H T, Knight C G, Barrett A J: Colorimetric and fluorimetric microplate assays for legumain and a staining reaction for detection of the enzyme after electrophoresis. Anal Biochem. 1999; 273(2):278-283). In brief, samples (20 μL) were added to black 96-well microplates (Corning Life Science, Lowell, Mass., USA) followed by 100 μL of legumain assay buffer pH 5.8 (1 mM DTT, 39.5 mM citric acid, 121 mM $Na_2HPO_4$, 1 mM $Na_2EDTA$, 0.01% c CHAPS; Sigma Aldrich) and 50 μL of the substrate solution (final concentration 10 μM). Immediately after the addition of substrate, kinetic measurements based on the increase in fluorescence over 30 min was performed at 30° C. in a plate reader Wallac Victor 3 (PerkinElmer, Waltham, Mass., USA). Filters were 360 nm for excitation and 460 nm for emission.

Quenching refers to any process that decreases the fluorescence intensity of a given substance. A variety of processes can result in quenching and due to the brownish color of the material the effect of quenching was taken under consideration. In order to correct for potential quenching by the colored extracts, a fluorescent group, N-AMC (Bachem AG), was added to the samples of unfractionated ANDOSAN™ or the different fractions before the fluorescence was measured in a plate reader Wallac Victor 3 (PerkinElmer).

Statistical Analysis

Analysis of significant differences was performed by paired t-test using Minitab Version 16 Statistical Software (Minitab Inc, Pennsylvania, USA). Differences were considered significant when $p<0.05$. Spearman's rank order correlation was used to evaluate dose- or time-dependency and $p<0.05$ was considered significant.

Figure 3A:
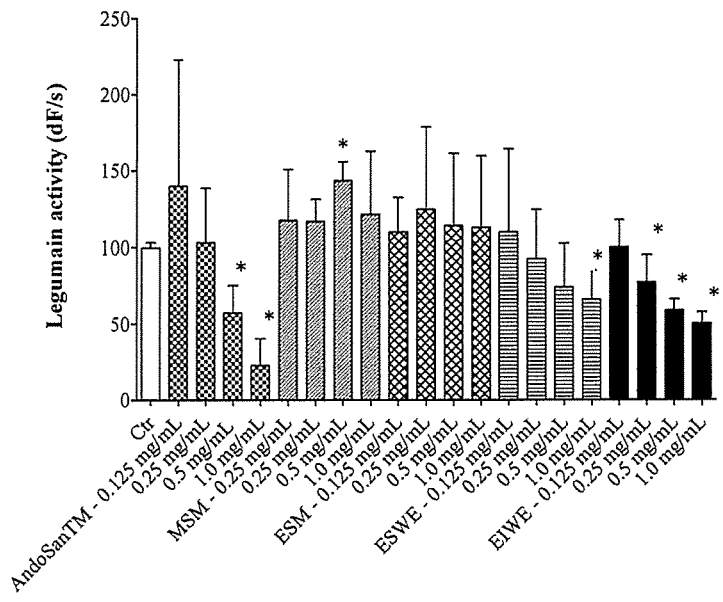
FIGS. 3A-B: Effects of various extracts of ANDOSAN™ on legumain activity in rat macrophage cell line RAW 264.7 cells. RAW 264.7 cells were incubated for 48 h in the absence or presence of various concentrations of A: unfractionated ANDOSAN™, MSM, ESM, ESWE or EIWE (0.125, 0.25, 0.5 or 1.0 mg/mL) and B: EIWE, EIWE-A or EIWE-B (0.125, 0.25 or 0.5 mg/mL). Legumain activity [change in fluorescence per second (dF/s)] in the various lysates was measured using a fluorogenic peptide substrate as described in the Examples and shown in percent of control. Parallel incubations were performed for each polysaccharide, and samples were run in duplicates. The data are given as mean±SD of three separate experiments. Activity bars denoted * are significantly different from the control (p<0.05) according to the paired t-test. (ESM—ethanol soluble material; ESWE—ethanol soluble water extract; MSM—methanol soluble material)
Figure 3B:
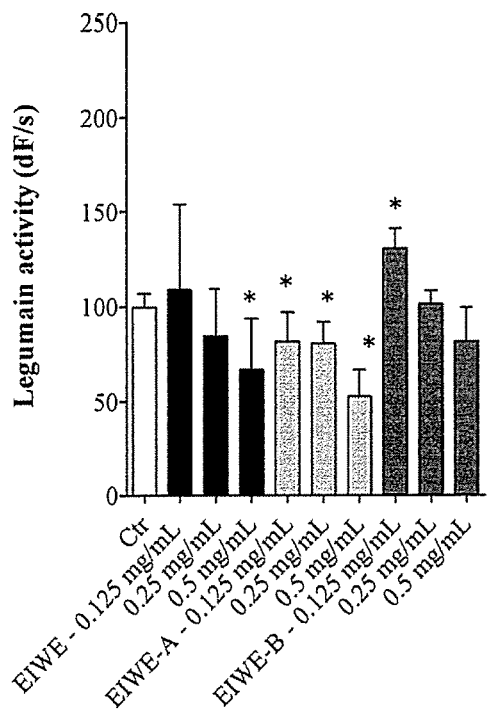

Effects of Various Fractions of ANDOSAN™ on Legumain Activity in RAW 264.7 Cells RAW 264.7 cells were incubated for 48 h in the presence of various concentrations (0.125, 0.25, 0.5 or 1.0 mg/mL) of unfractionated ANDOSAN™, MSM, ESM, ESWE or EIWE. Incubation with unfractionated ANDOSAN™ significantly reduced the legumain activity in a dose-dependent manner (rho=−0.778, $p<0.01$) and by up to 80% of the control at the highest concentration ($p<0.01$). ESWE at 1 mg/mL and EIWE at 0.25, 0.5 and 1 mg/mL also reduced the legumain activity ($p<0.018$) but to a lesser extent than unfractionated ANDOSAN™. ESWE showed weaker dose-dependent correlations (rho=−0.446 p=0.0138) than ANDOSAN™ whereas EIWE did not show statistically significant dose-dependent activity (rho=0.0438, p=0.816). Incubation with 0.5 mg/ml MSM resulted in a slightly increased legumain activity, compared to control ($p<0.01$), whereas ESM and the remaining concentrations of the other fractions had no significant effect on the legumain activity level (FIG. 3A). The extract fraction exhibiting the most potent inhibition of legumain activity was EIWE, which was further fractionated into EIWE-A and EIWE-B, as described above. RAW 264.7 cells were incubated for 48 h in the presence of various concentrations (0.125, 0.25 or 0.5 mg/mL) of EIWE, EIWE-A or EIWE-B. Incubation with EIWE-A gave significant dose-dependent reductions (rho=−0.782, $p<0.01$) in legumain activity and significant reductions in legumain activity compared to the control ($p<0.05$). Moreover, EIWE-B did not show significant dose-dependent reduction in legumain activity (rho=−0.380, p=0.0663), and measured effects were not significantly lower than the control; on the contrary, incubation with 0.125 mg/mL EIWE-B resulted in a slight increase in legumain activity ($p<0.01$) (FIG. 3B).

According to previous observations, LPS inhibits legumain activity in RAW 264.7 cells (Berven, L. et al. Biochimie 2013), thus, all fractions were checked for LPS contamination by adding polymyxin B (10 μg/mL) to the cells in addition to the different fractions. No change in legumain activity was observed after polymyxin B treatment, indicating that the inhibiting effect was due to active components in ANDOSAN™ other than LPS.

Example 4. Inhibition of Active Legumain by Unfractionated and Fractionated ANDOSAN™

Figure 4:
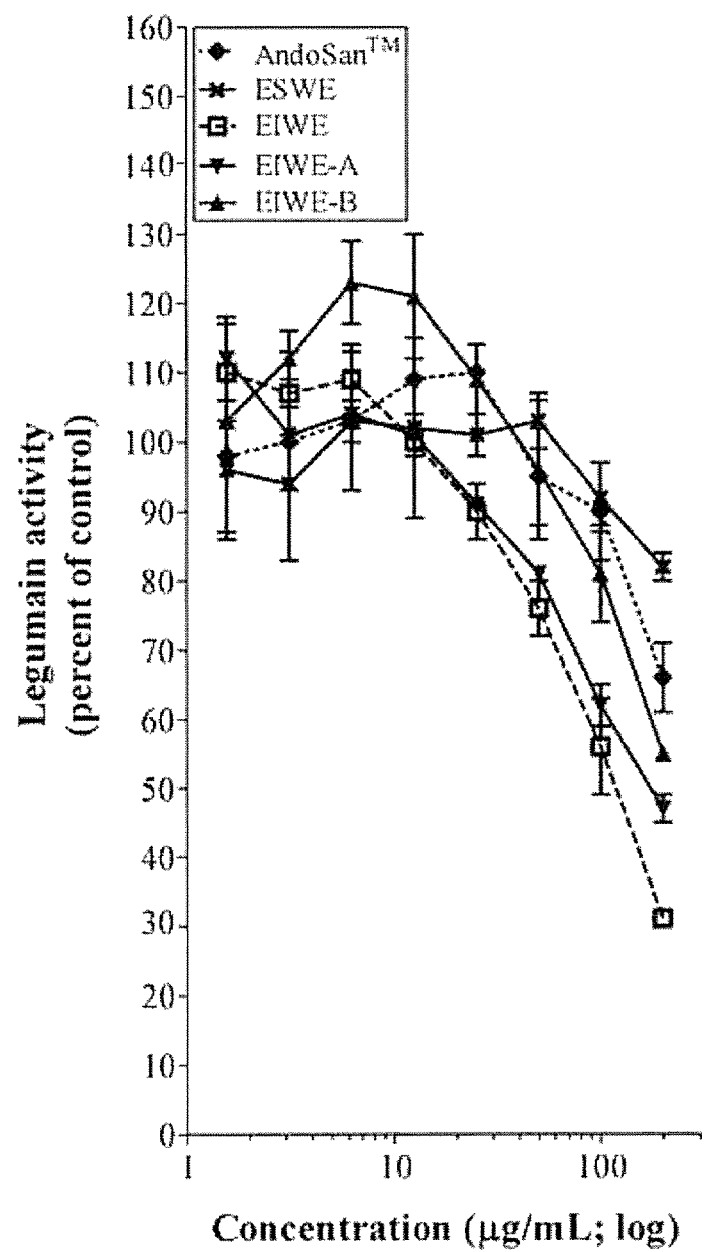
FIG. 4: Inhibition of active legumain by ANDOSAN™. Active legumain was incubated for 30 minutes at pH 5.5 in the presence of increasing concentrations (1.5, 3, 6, 12.5, 25, 50, 100, 200 µg/mL in incubate) of ANDOSAN™, ESWE, EIWE, EIWE-A or EIWE-B. Legumain activity (dF/s) in the various incubates is shown in percent of control (absence of ANDOSAN™). Samples were run in duplicates and results from one representative experiment are shown (n=2).

Legumain activity was measured after 30 min incubation of legumain in the presence of increasing concentrations (1.5, 3, 6, 12.5, 25, 50, 1(00) and 200 μg/mL in incubates) of unfractionated ANDOSAN™, MSM (not shown), ESM (not shown). ESWE, EIWE, EIWE-A or EIWE-B (FIG. 4). A reduction in legumain activity was observed for EIWE, EIWE-A and EIWE-B at concentrations increasing from 6.25 to 200 μg/mL (and a maximal 69, 53 and 45% reduction, respectively, was observed at 200 μg/mL, compared to control. Whereas ESWE reduced the legumain activity with only 18% at 200 μg/mL, incubation with 200 μg/mL unfractionated ANDOSAN™, ESM or MSM resulted in a 34%, 19% and 13% inhibition of legumain activity, respectively. ESWE, MSM and ESM concentrations below 50 μg/mL and unfractionated ANDOSAN™ concentrations below 25 μg/mL had no effect on the legumain activity. Substitution of Z-Ala-Ala-Asn-AMC with a fluorescent group (N-AMC) demonstrated that the colored extracts did not provide quenching (not shown).

Example 5. Inhibition of Prolegumain Autoactivation by Unfractionated and Fractionated ANDOSAN™

Figure 5A:
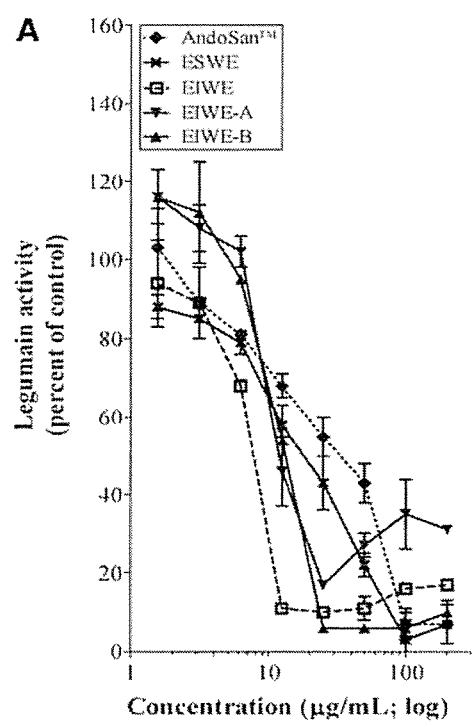
FIGS. 5A-B: Autoactivation of prolegumain is inhibited by ANDOSAN™. A: Prolegumain (200 ng/mL) was incubated at pH 4.0 and 37° C. for 4 h in the absence (control) or presence of increasing concentrations (1.5, 3, 6, 12.5, 25, 50, 100, 200 µg/mL in incubate) of unfractionated ANDOSAN™, ESWE, EIWE, EIWE-A or EIWE-B. Legumain activity (dF/s) in the various incubates is shown in percent of control. Samples were run in duplicates and results from one representative experiment are shown (n=3). B: Prolegumain was incubated for up to 6 hours at pH 4.0 at 37° C. in the absence (control) or presence of unfractionated ANDOSAN™, ESWE, EIWE, EIWE-A or EIWE-B (200 µg/mL in incubate). Legumain activity (dF/s) in the various incubates is shown. Samples were run in duplicates and results from one representative experiment are shown (n=3).
Figure 5B:
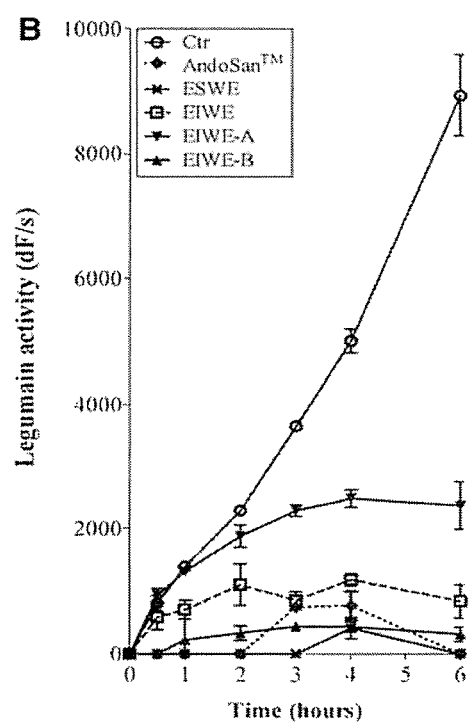

Legumain activity was measured after 4 h incubation of prolegumain at pH 4.0 and 37° C. in the presence of increasing concentrations (1.5, 3, 6, 12.5, 25, 50, 100 and 200 µg/mL in incubates) of unfractionated ANDOSAN™, MSM, ESM, ESWE, EIWE, EIWE-A or EIWE-B. A maximal 94%, 90% and 83% reduction in legumain activity was registered for EIWE-B, EIWE and EIWE-A, respectively at 25 µg/mL, compared to control. Further increase in EIWE and EIWE-B concentrations had no additional effect on the legumain activity level, whereas EIWE-A concentrations above 25 µg/mL resulted in a slight increase in legumain activity. A dose-dependent reduction in legumain activity was observed for ESWE, unfractionated ANDOSAN™, ESM (not shown) and MSM (not shown) (97%, 93%, 84% and 76% reduction, respectively, at 200 µg/mL, compared to control; FIG. 5 A). Furthermore, unfractionated ANDOSAN™, MSM, ESM, ESWE, EIWE, EIWE-A and EIWE-B (200 µg/mL in incubates) were found to directly inhibit prolegumain autoactivation in a time-dependent manner at pH 4.0 and 37° C. (FIG. 5B). One hour incubation of prolegumain with ANDOSAN™, ESWE, ESM (not shown), EIWE-B or EIWE resulted in a lower legumain activity (100%, 100%, 87%, 84% and 49% reduction, respectively) compared to control. Furthermore, 2 h incubation with MSM (not shown) and 3 h incubation with EIWE-A resulted in a significantly lower (p<0.01) legumain activity (51% and 37% reduction, respectively) compared to control. Further incubation up to 6 h resulted in minor additional effects on the activation levels compared to control.

Figures 7A, 7B:
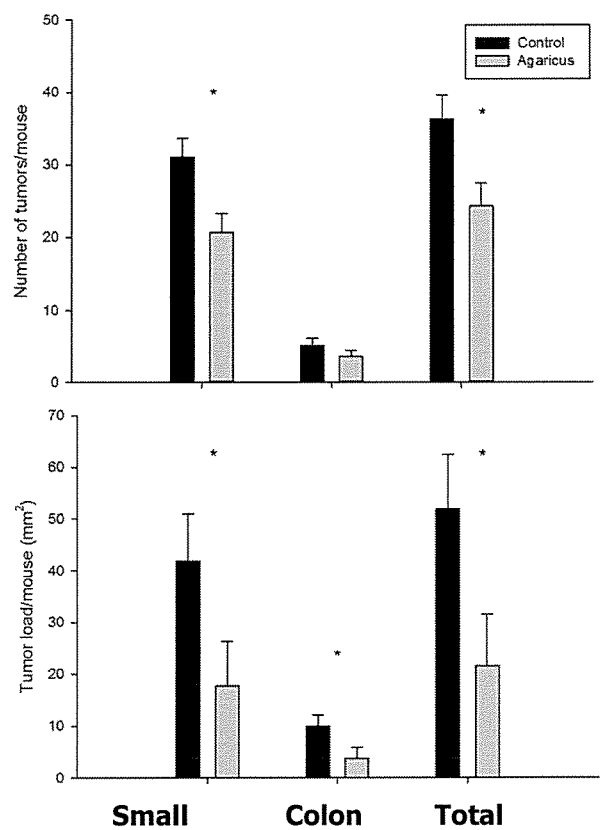
FIG. 7A-B: ANDOSAN™ protects against intestinal and colon cancer in A/J Min/+ mice. ANDOSAN™ (10%) was added or not added to drinking water for A/J Min/+ mice for 22 weeks. The animals were sacrificed and their intestines microscoped. There was both a lower number of tumors (A) and lower tumor load (=#tumor×size) (B) in the ANDOSAN™ relative to the control group.
Figure 8A:
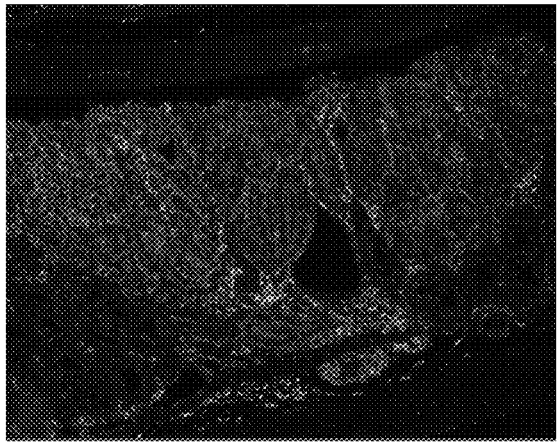
FIGS. 8A-D are pictures of the tumor-associated enzyme, legumain, in intestines of (A) untreated A/J Min/+ control mice and (B) ANDOSAN™ treated A/J Min/+ mice.
Figure 8B:
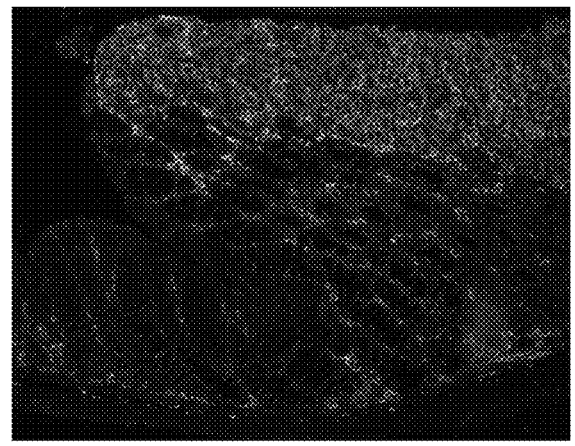
Figure 8C:
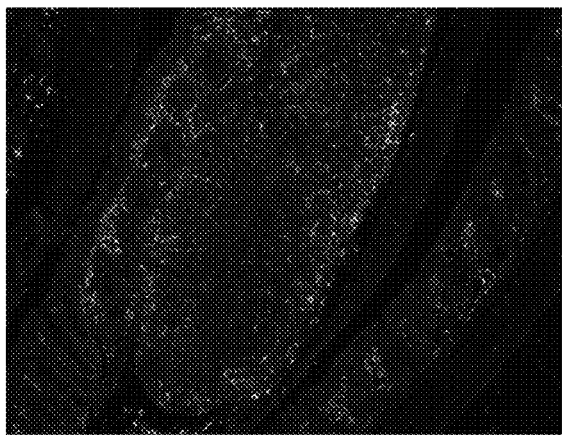
Figure 8D:
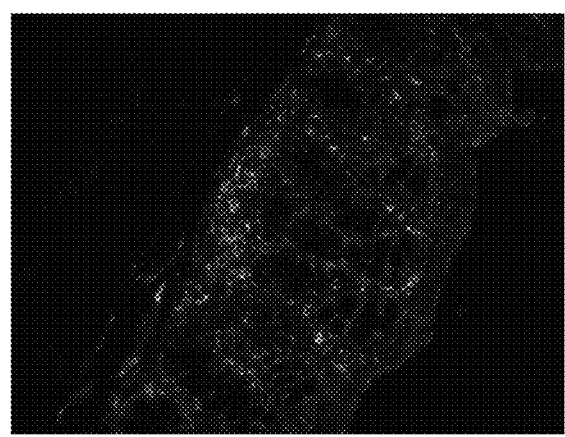

Example 6. Influence of ANDOSAN™ on the Development of Adenomatous Tumors in Small Intestines and Colon/Rectum of A/J Min/+ Mice The influence of the AbM-based ANDOSAN™ extract on the development of adenomatous tumors in small intestines and the colon/rectum of A/J Min/+ mice when added to the drinking water was determined. The effect of the AbM-based ANDOSAN™ extract on the intestinal concentration of the inflammatory and tumor-associated enzyme, legumain was also determined. Serum cytokine levels were measured and the putative cytotoxic effect of the mushroom extract on the human colon cancer cell line, CaCo2 was also examined.
Cytotoxic Effect of ANDOSAN™ In Vitro on Human Cancer Coli Cell Line The in vitro antitumor effect of ANDOSAN™ was examined in cultures of CaCo2 cells after 96 h. There was a dose-dependent cytotoxic effect (Spearman's (non-parametrisk) correlation coefficient rho) ($\rho=-0.986$, $p=0.0000002$) of the mushroom extract on this colon carcinoma cell line (FIG. 6). Whereas a concentration of 5% of ANDOSAN™ induced killing of nearly 90% of the CaCo2 cells (two-tailed t-test, p=0.0000000596), even 0.5% of ANDOSAN™ had a significant albeit low (14%) cytotoxic effect (two-tailed t-test, p=0.00612). The mechanism of death was apoptosis (data not shown).
Antitumor Effect of ANDOSAN™ In Vivo on AJ/Min+/- Mice In A/J Min/+ mice given 10% of ANDOSAN™ in their drinking (tap) water for 22 weeks, on average 23 tumors/mouse was found in their intestines by microscopy of the formalin preserved intestines. This was statistically significantly (p=0.0210) fewer tumors than the average 37 tumors/mouse counted in the intestines of such mice given drinking (tap) water without ANDOSAN™ (FIG. 7a). The microscopy was done in a blinded fashion in such a way that the treatment group of the individual mouse examined, was unknown to the pathologist. When the size of the tumors was noted and multiplied with the number of tumors, there was an approximately 60% significant reduction in the tumor load in both small intestines (p=0.0004) and colon/rectum (p=0.0235) of the ANDOSAN™ treated mice relative to the tumor load in the control animals (FIG. 7b). Similar but less pronounced findings were done in intestines of animals treated for 15 weeks with or without ANDOSAN™ (data not shown). Since there was no difference in body weight between the groups, ANDOSAN™ in drinking water did not affect water or feed intake and should therefore not bias the results.
Effect on Legumain Concentration in Intestines When cross-sections of intestines were immuno-fluorescence-stained for legumain and microscoped, there was a smaller amount of this metastasis-promoting enzyme in intestines from the ANDOSAN™ treated animals (FIGS. 8a and 8b).
Serum Cytokine Profiles in A/J Min/+ and Wild-Type Mice Sera of both A/J Min/+ mice and wild-type controls that had been sacrificed by exsanguination, were subjected to Luminex multi(23-)plex analysis for Th1, Th2, Th17, pro- and anti-inflammatory cytokines. There were no differences in serum cytokine levels between treated and untreated A/J Min/+ mice, and no correlations between cytokine level and tumor load. However, there was a significant increase in the pro-inflammatory cytokine levels for ANDOSAN™ treated wild-type mice compared with untreated ones, an effect that was not seen for the A/J Min/+ mice (FIG. 4).

The invention claimed is:
1. A method for treating tumors associated with increased activity of legumain, comprising determining if a patient has a tumor associated with increased activity of legumain, administering to a patient suffering from such a tumor, an isolated, polar, high molecular weight fraction of an *Agaricus blazei* Murill extract in combination with a pharmaceutically acceptable carrier or excipient, wherein said isolated, polar, high molecular weight fraction of an *Agaricus blazei* Murill extract is produced by:
    (a) extracting a lyophilized aqueous preparation of fermented *Agaricus blazei* Murill with dichloromethane, to obtain a dichloromethane-insoluble material as a first residue;
    (b) extracting said first residue obtained in (a) with methanol to obtain a methanol-insoluble material as a second residue;
    (c) extracting said second residue obtained in (b) with a concentrated aqueous solution of ethanol, to obtain an ethanol-insoluble material as a third residue;
    (d) dissolving said third residue in water and further fractionating it by size, and
    (e) isolating a fraction comprising polar, high molecular weight compounds, wherein said polar, high molecular weight compounds have an average molecular weight of about 50 kDa, as determined using oat β-glucan standards.
2. The method according to claim 1, wherein said isolated, polar, high molecular weight fraction of an *Agaricus blazei* Murill extract is administered in combination with extracts of *Hericium erinaceum* and/or *Grifola frondosa*.
3. The method according to claim 1, wherein said patient is suffering from a solid tumor or a hematological cancer.
4. The method according to claim 3, wherein said patient is suffering from a solid tumor.
5. The method according to claim 1, wherein said isolated, polar, high molecular weight fraction of an *Agaricus blazei* Murill extract is administered orally or parenterally.

6. A method for inhibiting legumain, comprising administering to a patient in need of such inhibiting, an isolated, polar, high molecular weight fraction of an *Agaricus blazei* Murill extract in an amount sufficient to inhibit legumain activity, in combination with a pharmaceutically acceptable carrier or excipient, wherein said isolated, polar, high molecular weight fraction of an *Agaricus blazei* Murill extract is produced by:
 (a) extracting a lyophilized aqueous preparation of fermented *Agaricus blazei* Murill with dichloromethane, to obtain a dichloromethane-insoluble material as a first residue;
 (b) extracting said first residue obtained in (a) with methanol to obtain a methanol-insoluble material as a second residue;
 (c) extracting said second residue obtained in (b) with a concentrated aqueous solution of ethanol, to obtain an ethanol-insoluble material as a third residue;
 (d) dissolving said third residue in water and further fractionating it by size, and
 (e) isolating a fraction comprising polar, high molecular weight compounds, wherein said polar, high molecular weight compounds have average molecular weight of about 50 kDa, as determined using oat β-glucan standards.

7. A method for activating natural killer cell activity and mediating apoptosis of cancer cells, comprising administering to a patient in need of such treatment, an isolated, polar, high molecular weight fraction of an *Agaricus blazei* Murill extract, wherein said isolated, polar, high molecular weight fraction of an *Agaricus blazei* Murill extract is produced by:
 (a) extracting a lyophilized aqueous preparation of fermented *Agaricus blazei* Murill with dichloromethane, to obtain a dichloromethane-insoluble material as a first residue;
 (b) extracting said first residue obtained in (a) with methanol to obtain a methanol-insoluble material as a second residue;
 (c) extracting said second residue obtained in (b) with a concentrated aqueous solution of ethanol, to obtain an ethanol-insoluble material as a third residue;
 (d) dissolving said third residue in water and further fractionating it by size, and
 (e) isolating a fraction comprising polar, high molecular weight compounds, wherein said polar, high molecular weight compounds have an average molecular weight of about 50 kDa, as determined using oat β-glucan standards.

8. The method according to claim 6, wherein said isolated, polar, high molecular weight fraction of an *Agaricus blazei* Murill extract is administered in combination with extracts of *Hericium erinaceum* and/or *Grifola frondosa*.

9. A method for inhibiting legumain in a patient suffering from atherosclerosis or inflammation, comprising administering to the patient in need of such inhibiting, an isolated, polar, high molecular weight fraction of an *Agaricus blazei* Murill water extract in an amount sufficient to inhibit legumain, in combination with a pharmaceutically acceptable carrier or excipient, wherein said isolated, polar, high molecular weight fraction of an *Agaricus blazei* Murill extract comprises polar, high molecular weight compounds, wherein said polar, high molecular weight compounds have an average molecular weight of about 50 kDa and are insoluble in dichloromethane, methanol and ethanol.

10. A method for inhibiting legumain in a patient comprising administering to a patient in need of such inhibiting, an isolated, polar, high molecular weight fraction of an *Agaricus blazei* Murill water extract in an amount sufficient to inhibit legumain, in combination with a pharmaceutically acceptable carrier or excipient, wherein said isolated, polar, high molecular weight fraction of an *Agaricus blazei* Murill extract comprises polar, high molecular weight compounds, wherein said polar, high molecular weight compounds have an average molecular weight between about 35.6-70.6 kDa and are insoluble in dichloromethane, methanol and ethanol.

* * * * *